(12) United States Patent
Cushman et al.

(10) Patent No.: US 9,801,861 B2
(45) Date of Patent: Oct. 31, 2017

(54) ANTIMICROBIAL SUBSTITUTED THIAZOLES AND METHODS OF USE

(71) Applicant: Purdue Research Foundation, West Lafayette, IN (US)

(72) Inventors: Mark Stanley Cushman, West Lafayette, IN (US); Mohamed Seleem, West Lafayette, IN (US); Abdelrahman S Mayhoub, Giza (EG)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/142,008

(22) Filed: Apr. 29, 2016

(65) Prior Publication Data

US 2016/0243088 A1  Aug. 25, 2016

Related U.S. Application Data

(62) Division of application No. 14/069,089, filed on Oct. 31, 2013, now Pat. No. 9,353,072.

(60) Provisional application No. 61/720,659, filed on Oct. 31, 2012.

(51) Int. Cl.

| | | |
|---|---|---|
| *A61K 31/426* | (2006.01) | |
| *C07D 277/28* | (2006.01) | |
| *C07D 277/30* | (2006.01) | |
| *C07D 417/04* | (2006.01) | |
| *C07D 277/24* | (2006.01) | |

(52) U.S. Cl.
CPC .......... *A61K 31/426* (2013.01); *C07D 277/24* (2013.01); *C07D 277/28* (2013.01); *C07D 277/30* (2013.01); *C07D 417/04* (2013.01)

(58) Field of Classification Search
CPC .............. A61K 31/426; C07D 277/28
See application file for complete search history.

(56) References Cited

U.S. PATENT DOCUMENTS

| | | | | |
|---|---|---|---|---|
| 6,232,290 B1* | 5/2001 | Ohki | ........................ | C07K 7/56 514/2.3 |
| 2004/0009877 A1* | 1/2004 | Fischer | .................. | A01N 43/78 504/266 |
| 2008/0200445 A1* | 8/2008 | Zhu | ...................... | C07D 233/88 514/210.02 |

FOREIGN PATENT DOCUMENTS

WO   WO 2012115118   *   8/2012  ............... C07K 7/56

OTHER PUBLICATIONS

Mayhoub et al. (Bioorg. Med. Chem. 19 (2011) 3845-3854).*
Kayakiri et al. (Machine Translation of WO 2012115118, Aug. 2012).*
Mhaske, et al., Synthesis, Characterization, and Anti Microbial Activity of 3'-(4-(2-Substituted thiazol-4-yl)phenyl)spiro [indoline-3,2'-thiazoldine]-2,4'-diones, J. Hetrocyclic Chem., 47, 1415-20, (2010).
Shelke, et al., Synthesis and antimicrobial activities of novel series of 1-((4-methyl-2-substituted thiazol-5-yl) methyleneamino)-2-substituted isothiourea serivatives, Department of Chemistry Dir Parshurambhau College, DOI:10.1080/10426507.2012.745542 (2012).
Shelke, et al., Synthesis and antimicrobial activities of novel series of 3-aryl-2-(2-substituted-4-methylthiazole-5yl) thiazofidin-4-one as possible anti-inflammatory and antimicrobial agents, Bioorg. Med. Chem. Lett. 22 (2012) 6373-76.
CAS/STN Registry # 464154-31-2 (Entered STN: Oct. 23, 2002).
Simiti et al. (CAPLUS Abstract of: Archly der Pharmazie (Weinheim, Germany) (1981), 314(9), 744-50).
Burger et al. (CAPLUS Abstract of: Synthesis (1990), (4), 360-5).
Kulkarni et al. (CAPLUS Abstract of: Journal of Scientific & Industrial Research (1959), 18B, 376-8).

* cited by examiner

*Primary Examiner* — Robert Havlin
(74) *Attorney, Agent, or Firm* — Valauskas Corder LLC

(57) ABSTRACT

Disclosed are compositions having activity against MRSA and/or VRSA, and methods of using the compositions to treat microbial infections.

10 Claims, 10 Drawing Sheets

Table 1. Strains of *Staphylococcus aureus* used in this study.

| NARSA Strain ID | Strain Name Alternate Designation | Isolation Origin | Year | SCCmec type | Molecular Typing spa type | Phenotypic Properties |
|---|---|---|---|---|---|---|
| — | ATCC 43300 | United States (Kansas) | — | — | — | Resistant to methicillin |
| NRS1 | ATCC 700699 | Japan | 1996 | II | TJMBMDMGMK | Resistant to aminoglycosides and tetracycline (minocycline). Glycopeptide-intermediate *Staphylococcus aureus* |
| NRS19 | VISA, HIP7256 | United States (Illinois) | 1999 | II | TJMBMDMGMK | Glycopeptide-intermediate *Staphylococcus aureus* |
| NRS37 | VISA, LIM3 | France | 1995 | I | YHGFMBQBLO | Glycopeptide-intermediate *Staphylococcus aureus* |
| NRS107 | BK2529 | United States | — | — | YKGFMBQBLO | Resistant to vancomycin |
| NRS108 | A980649 | France | — | — | YKGFMBQBLO | Resistant to gentamicin |
| NRS119 | SA LinR #12 | United States (Massachusetts) | 2001 | — | YHGCMBQBLO | Resistant to linezolid |
| NRS112 | USA400 | United States (North Dakota) | 1998 | IV | UJFKBPE | Resistant to methicillin, susceptible to non beta-lactam antibiotics |
| NRS194 | C1999000529 | United States (North Dakota) | 1999 | IV | UJFKKPKHE | Resistant to methicillin |
| NRS382 | USA100 | United States (Ohio) | — | II | TJMBMDMGMK | Resistant to ciprofloxacin, clindamycin, erythromycin, and methicillin |
| NRS383 | USA200 | United States (North Carolina) | — | II | WGKAOKQQQ | Resistant to ciprofloxacin, clindamycin, erythromycin, gentamicin, and methicillin |
| NRS384 | USA300-0114 | United States (Mississippi) | — | IV | YHGFMBQBLO | Resistant to erythromycin, methicillin, and tetracycline |
| NRS385 | USA500 | United States (Connecticut) | — | IV | YHGCMBQBLO | Resistant to ciprofloxacin, clindamycin, erythromycin, gentamicin, methicillin, tetracycline, and trimethoprim |
| NRS386 | USA700 | United States (Louisiana) | — | IV | UJGFMGGM | Resistant to erythromycin and methicillin |
| NRS387 | USA800 | United States (Washington) | — | IV | TJMEMDMGGMK | Resistant to methicillin |
| NRS483 | USA1000 | United States (Vermont) | — | IV | — | Resistant to erythromycin and methicillin |
| NRS484 | USA1100 | United States (Alaska) | — | IV | — | Resistant to methicillin |
| VRS10 | VRSA | United States (Michigan) | 2009 | — | — | Resistant to ciprofloxacin, clindamycin, erythromycin, gentamicin, and vancomycin |

NARSA = Network on Antimicrobial Resistance in *Staphylococcus aureus*.

FIG. 6

TABLE 2

*Antimicrobial activities (Minimum Inhibitory Concentration (mg/L) and structures of modified thiazole compounds screened against Staphylococcus aureus.*

Minimum Inhibitory Concentration (mg/L) of Thiazole Compounds and Vancomycin Against *S. aureus*

| Strains | 1a | 1c | 1d | 1e |
|---|---|---|---|---|
| MRSA ATCC 43300 | 2.8 | 1.2 | 0.5 | 3.0 |
| MRSA ATCC 700699 | 1.4 | 2.3 | 0.5 | 0.7 |
| VISA HIP07256 | 1.4 | 2.3 | 0.5 | 1.5 |
| VISA LIM 3 | 1.4 | 1.2 | 0.5 | 0.7 |
| NRS107 | 1.4 | 1.2 | 0.5 | 0.7 |
| NRS108 | 1.4 | 1.2 | 1.1 | 3.0 |
| NRS119 | 1.4 | 2.3 | 1.1 | 1.5 |
| MRSA USA400 | 1.4 | 1.2 | 1.1 | 1.5 |
| NRS194 | 1.4 | 2.3 | 1.1 | 3.0 |
| MRSA USA100 | 5.5 | 1.2 | 1.1 | 1.5 |
| MRSA USA200 | 2.8 | 2.3 | 1.1 | 1.5 |
| MRSA USA300 | 1.4 | 1.2 | 1.1 | 3.0 |
| MRSA USA500 | 1.4 | 2.3 | 1.1 | 3.0 |
| MRSA USA700 | 1.4 | 1.2 | 1.1 | 3.0 |
| MRSA USA800 | 2.8 | 2.3 | 0.5 | 1.5 |
| MRSA USA1000 | 1.4 | 1.2 | 1.1 | 3.0 |
| MRSA USA1100 | 2.8 | 1.2 | 1.1 | 1.5 |
| VRSA | 1.4 | 1.2 | 1.1 | 3.0 |

FIG. 7A

TABLE 2-continued

Minimum Inhibitory Concentration (mg/L) of Thiazole Compounds and Vancomycin Against S. aureus

| Strains | 1f | 1g | 1h | 7 |
|---|---|---|---|---|
| MRSA ATCC 43300 | 2.2 | 1.9 | 3.8 | 1.2 |
| MRSA ATCC 700699 | 1.1 | 1.9 | 3.8 | 0.6 |
| VISA HIP07256 | 2.2 | 1.9 | 1.9 | 0.6 |
| VISA LIM 3 | 1.1 | 1.9 | 1.9 | 0.6 |
| NRS107 | 1.1 | 1.0 | 1.9 | 0.6 |
| NRS108 | 4.4 | 1.9 | 1.9 | 2.3 |
| NRS119 | 2.2 | 1.9 | 3.8 | 0.6 |
| MRSA USA400 | 4.4 | 1.9 | 1.9 | 0.6 |
| NRS194 | 4.4 | 1.9 | 1.9 | 0.6 |
| MRSA USA100 | 2.2 | 1.0 | 1.9 | 1.2 |
| MRSA USA200 | 2.2 | 1.9 | 1.9 | 1.2 |
| MRSA USA300 | 2.2 | 1.0 | 1.9 | 1.2 |
| MRSA USA500 | 4.4 | 1.0 | 1.9 | 1.2 |
| MRSA USA700 | 2.2 | 1.0 | 1.9 | 1.2 |
| MRSA USA800 | 2.2 | 1.0 | 1.9 | 0.6 |
| MRSA USA1000 | 2.2 | 1.0 | 1.9 | 0.6 |
| MRSA USA1100 | 2.2 | 1.9 | 1.9 | 0.6 |
| VRSA | 2.2 | 1.0 | 0.5 | 1.2 |

FIG. 7B

TABLE 2-continued

Minimum Inhibitory Concentration (mg/L) of Thiazole Compounds and Vancomycin Against *S. aureus*

| Strains | 8 | 12 | VAN |
|---|---|---|---|
| MRSA ATCC 43300 | 1.5 | 0.6 | 0.7 |
| MRSA ATCC 700699 | 0.7 | 0.6 | 2.9 |
| VISA HIP07256 | 0.7 | 0.6 | 2.9 |
| VISA LIM 3 | 0.4 | 0.6 | 2.9 |
| NRS107 | 0.7 | 1.2 | 0.7 |
| NRS108 | 1.5 | 2.4 | 0.7 |
| NRS119 | 0.7 | 0.6 | 1.4 |
| MRSA USA400 | 0.7 | 0.6 | 0.7 |
| NRS194 | 0.7 | 1.2 | 0.7 |
| MRSA USA100 | 0.7 | 2.4 | 1.4 |
| MRSA USA200 | 1.5 | 0.6 | 0.4 |
| MRSA USA300 | 0.7 | 1.2 | 0.7 |
| MRSA USA500 | 0.7 | 1.2 | 0.7 |
| MRSA USA700 | 1.5 | 0.6 | 0.7 |
| MRSA USA800 | 0.7 | 1.2 | 0.7 |
| MRSA USA1000 | 0.7 | 0.6 | 0.7 |
| MRSA USA1100 | 0.7 | 0.6 | 0.7 |
| VRSA | 1.5 | 1.2 | 185.5 |

Numbers (1a-12) correspond to the sequence in which the compounds were synthesized. VAN = Vancomycin, VISA = Vancomycin-intermediate *Staphylococcus aureus*, VRSA = Vancomycin-resistant *Staphylococcus aureus*.

ANTIMICROBIAL SUBSTITUTED THIAZOLES AND METHODS OF USE

CROSS-REFERENCE TO RELATED APPLICATIONS

This application is a division application of U.S. patent application Ser. No. 14/069,089 filed Oct. 31, 2013, which claims the benefit of priority to U.S. Provisional Patent Application No. 61/720,659 filed Oct. 31, 2012, both incorporated by reference in their entireties.

BACKGROUND OF THE INVENTION

Methicillin-resistant *Staphylococcus aureus* (MRSA) is a rapidly expanding global health concern; it is currently the most common pathogen linked to patients with skin and soft-tissue infections. Apart from the high mortality and rapid transmission rates, MRSA infections result in billions of dollars in additional health care costs each year. Several recent studies have indicated a steady decline in the number of health care-associated invasive MRSA infections (infections contracted by a patient admitted in a hospital or clinic for another health-related issue) both in the United States and Europe. Although there has been a decrease in invasive health care-associated MRSA infections that can be attributed to greater awareness and implementation of MRSA prevention programs, community-associated MRSA (CA-MRSA) infections remain a significant threat to the general public. Compounding the problem further is the limited number of effective antimicrobials commercially available to treat MRSA infections.

A number of antimicrobials which were once deemed effective against MRSA have now become ineffective due to the development of microbial resistance to these agents. MRSA isolates resistant to a wide-variety of antimicrobial drug classes including the β-lactam antibiotics (namely the penicillins and cephalosporins), macrolides, and fluoroquinolones have been found. Resistance has also emerged to therapeutic agents once deemed to be the drugs of choice in treating MRSA infections, such as vancomycin and linezolid.

There is an urgent need for compositions and methods for treating MRSA infections. The present invention addresses that demand.

SUMMARY OF THE INVENTION

The present invention relates generally to compositions and methods for treating infections by pathogenic bacteria.

In certain embodiments, the present invention provides a method of treating a microbial infection in a subject by administering to the subject a pharmaceutical composition that includes a compound having the chemical structure:

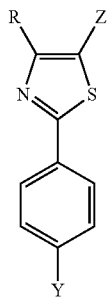

In certain embodiments, in the compound used in the method of the invention, Z is a cationic moiety and optionally includes a linker through which the cationic moiety is attached to the thiazole ring. Y is a lipophilic moiety, and R is H or any suitable substituent. Advantageously, the compound has antimicrobial activity. In certain embodiments, the compound does not substantially disrupt bacterial cell walls or membranes. The methods involve administering the pharmaceutical composition of the invention in an amount effective to inhibit growth of or kill the bacteria.

In certain embodiments, the cationic moiety is selected from aminoguanidinyls, primary amines, secondary amines, tertiary amines, primary aminoalkyls, secondary aminoalkyls, tertiary aminoalkyls, quaternary ammonium compounds, trialkylammoniumalkyls, guanidinyls, guanidinoalkyls, amidinoalkyls, and hydrazines.

In certain embodiments, Z further includes a linker. In certain embodiments, the linker may be an alkyl, alkenyl, alkynyl, or an aromatic moiety.

In certain embodiments, Y is an alkyl, cycloalkyl, aryl, cycloalkenyl, alkoxy, aryloxy, alkylthio, arylthio, amino, heteroaryl, acyl, phenyl, naphthyl, benzoyl, amide, heteroaryl, alkynyl, alkenyl, arylalkyl, arylalkynyl, arylalkenyl, haloalkyl, thioamide, nitro, ester, or carbamate.

In certain embodiments, R is an alkyl, alkenyl, alkynyl, aryl, heterocyclic, alkoxyl, alkylamino, alkythio, branched alkyl, dibromoalkyl, alkoxy, aryloxy, alkythio, amino, aryl, amide, carbamate, or heteroaryl, or is cyclized with the neighboring group to form a fused cyclic system.

In certain embodiments, the compounds may include Z, Y, and R groups chosen from the structures shown in the Supplemental Table of Compounds (Appendix A), in any possible combination of Z, Y, and R groups.

In certain embodiments, the compound has antimicrobial activity against one or more of a MRSA, a VRSA, a *Listeria monocytogenes*, a *Bacillus anthracis*, *Bacillus subtilis*, a *Bacillus cereus*, a *Mycobacterium*, a *Streptococcus pneumoniae*, a vancomycin-resistant *Enterococcus faecalis*, *Enterococcus faecium*, and a *Candida albicans*. In certain embodiments, the antimicrobial activity includes rapid killing of the microbe.

In certain embodiments is provided a compound having antimicrobial activity against MRSA having the structure:

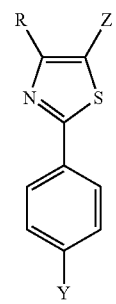

In which R is H or any suitable substituent, Z comprises a cationic moiety and optionally a linker through which the cationic moiety is attached to the thiazole ring, and Y is a lipophilic moiety, with the proviso that if Z comprises aminoguanidinyl, Y is not ethyl, propyl, butyl, or pentyl.

In certain embodiments, in the compound of the invention, Z is a cationic moiety and optionally includes a linker through which the cationic moiety is attached to the thiazole ring. Y is a lipophilic moiety, and R is H or any suitable substituent. Advantageously, the compound has antimicrobial activity. In certain embodiments, the compound does not substantially disrupt bacterial cell walls or membranes.

In certain embodiments, the cationic moiety is selected from aminoguanidinyls, primary amines, secondary amines, tertiary amines, primary aminoalkyls, secondary aminoalkyls, tertiary aminoalkyls, quaternary ammonium compounds, trialkylammoniumalkyls, guanidinyls, guanidinoalkyls, amidinoalkyls, and hydrazines.

In certain embodiments, Z further includes a linker. In certain embodiments, the linker may be an alkyl, alkenyl, alkynyl, or an aromatic moiety.

In certain embodiments, Y is an alkyl, cycloalkyl, aryl, cycloalkenyl, alkoxy, aryloxy, alkylthio, arylthio, amino, heteroaryl, acyl, phenyl, naphthyl, benzoyl, amide, heteroaryl, alkynyl, alkenyl, arylalkyl, arylalkynyl, arylalkenyl, haloalkyl, thioamide, nitro, ester, or carbamate.

In certain embodiments, R is an alkyl, alkenyl, alkynyl, aryl, heterocyclic, alkoxyl, alkylamino, alkythio, branched alkyl, dibromoalkyl, alkoxy, aryloxy, alkythio, amino, aryl, amide, carbamate, or heteroaryl, or is cyclized with the neighboring group to form a fused cyclic system.

In certain embodiments, the compounds may include Z, Y, and R groups chosen from the structures shown in the Supplemental Table of Compounds, in any possible combination of Z, Y, and R groups. In certain embodiments, the compound is provided as a pharmaceutically acceptable salt.

In certain embodiments, the compounds are provided as a pharmaceutical composition comprising a pharmaceutically acceptable carrier and one or more of the compounds or pharmaceutically acceptable salt thereof having antimicrobial activity against MRSA having the structure:

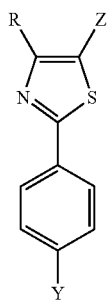

in which R is H or any suitable substituent, Z comprises a cationic moiety and optionally a linker through which the cationic moiety is attached to the thiazole ring, and Y is a lipophilic moiety.

In certain embodiments, in the compound of the pharmaceutical composition of the invention, Z is a cationic moiety and optionally includes a linker through which the cationic moiety is attached to the thiazole ring. Y is a lipophilic moiety, and R is H or any suitable substituent. Advantageously, the compound has antimicrobial activity. In certain embodiments, the compound does not substantially disrupt bacterial cell walls or membranes.

In certain embodiments, the cationic moiety is selected from aminoguanidinyls, primary amines, secondary amines, tertiary amines, primary aminoalkyls, secondary aminoalkyls, tertiary aminoalkyls, quaternary ammonium compounds, trialkylammoniumalkyls, guanidinyls, guanidinoalkyls, amidinoalkyls, and hydrazines.

In certain embodiments, Z further includes a linker. In certain embodiments, the linker may be an alkyl, alkenyl, alkynyl, or an aromatic moiety.

In certain embodiments, Y is an alkyl, cycloalkyl, aryl, cycloalkenyl, alkoxy, aryloxy, alkylthio, arylthio, amino, heteroaryl, acyl, phenyl, naphthyl, benzoyl, amide, heteroaryl, alkynyl, alkenyl, arylalkyl, arylalkynyl, arylalkenyl, haloalkyl, thioamide, nitro, ester, or carbamate.

In certain embodiments, R is an alkyl, alkenyl, alkynyl, aryl, heterocyclic, alkoxyl, alkylamino, alkythio, branched alkyl, dibromoalkyl, alkoxy, aryloxy, alkythio, amino, aryl, amide, carbamate, or heteroaryl, or is cyclized with the neighboring group to form a fused cyclic system.

In certain embodiments, the compounds may include Z, Y, and R groups chosen from the structures shown in the Supplemental Table of Compounds, in any possible combination of Z, Y, and R groups. The present invention and its attributes and advantages will be further understood and appreciated with reference to the detailed description below of presently contemplated embodiments, taken in conjunction with the accompanying drawings.

BRIEF DESCRIPTION OF THE DRAWINGS

FIG. 6 illustrates Table 1 listing bacterial strains presented in the study according to the invention.

FIG. 7A-C illstrates Table 2 listing antimicrobial activites and structures of modified thiazole compounds screened in the study according to the invention.

DETAILED DESCRIPTION OF THE INVENTION

Figure 1:
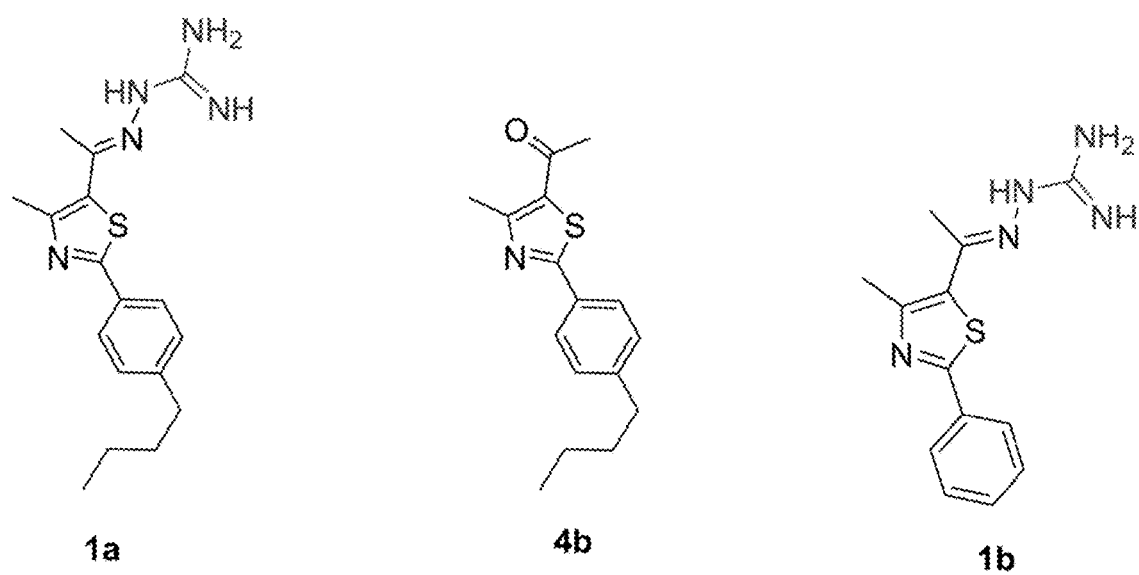
FIG. 1 shows the chemical structure of compound 1a and derivative compounds 4b and 1b.

In this study, whole-cell screening assays of libraries of substituted thiazoles and thiadiazoles provided a novel lead compound that displays notable antibacterial activity against MRSA. As can be seen with reference to FIG. 1, the lead compound 1a contains a thiazole central ring connected to two unique structural features—a cationic element at C5-position and a lipophilic tail at C2-position. It was then hypothesized that these two structural components may contribute to the antibacterial activity of the lead compound. Structural optimizations were focused on the lipophilic side chain of the lead compound in an attempt to enhance the antimicrobial activity of the lead compound against MRSA. Chemical modifications reported here involved building a focused library of phenylthiazoles with different lipophilic moieties at the phenyl-p-position to define the structure-activity-relationships (SARs) at the thiazole-C2 position.

Additionally, substitutions may be made to the cationic element at the C5 position. Such substitutions may include any suitable cationic moiety, provided antimicrobial activity against MRSA is maintained, and preferably, the compound does not cause substantial toxicity or disrupt the bacterial cell membrane. This study establishes that various thiazole compounds comprising an aminoguanidinyl moiety at the C-5 position have antimicrobial activity. Other thiazole derivatives that may have antimicrobial activity include those having primary amines, secondary amines, tertiary amines, primary aminoalkyls, secondary aminoalkyls, tertiary aminoalkyls, quaternary ammonium compounds, trialkylammoniumalkyls, guanidinyls, guanidinoalkyls, amidinoalkyls, or hydrazines at the C-5 position of the thiazole ring. See supplemental materials for structures of non-limiting examples of compounds suitable for use as antimicrobials.

The objectives of this study were to identify the antimicrobial activity of the thiazole derivatives against MRSA, vancomycin-resistant *S. aureus* (VRSA), and other pathogenic bacteria or yeast that cause infections that are difficult to treat, to ascertain the rate of clearance of MRSA in vitro by the lead compound and derivatives, to ensure the compounds meet solubility and permeability standards suitable for a drug-candidate as described by Lipinski's Rules of 5, to determine the cytotoxic impact of the derivatives in vitro, and to determine whether the mode of action of the derivatives involves disruption of the bacterial cell wall or cytoplasmic membrane.

Compounds found to have antimicrobial activity against MRSA and/or VRSA were tested for antimicrobial activity against the numerous bacterial species, including antibiotic resistant strains of bacterial species and against a pathogenic yeast strain. The compounds were found to have broad spectrum efficacy against numerous microorganisms. These include, but are not limited to, numerous strains of MRSA and VRSA, as well as *Listeria monocytogenes, Bacillus anthracis, Bacillus subtilis, Bacillus cereus, Mycobacterium, Streptococcus pneunomiae*, vancomycin-resistant *Enterococcus faecalis, Enterococcus faecium*, and *Candida albicans*.

The antimicrobials of the present invention may be formulated as a pharmaceutical composition suitable for administration by any suitable mode of administration, including, for example orally (e.g., enterally or sublingually), intravenously, intramuscularly, subcutaneously, transdermally, vaginally, rectally, intranasally, and the like.

In certain embodiments, the antimicrobials of the invention are prepared, purified, or formulated as a corresponding salt of the active compound or prodrug, for example, a pharmaceutically-acceptable salt. Examples of pharmaceutically acceptable salts are discussed in Berge, et al., J. Pharm. Sci., 66, 1-19 (1977). Unless otherwise specified, a reference to a particular compound also includes salt forms thereof. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In certain embodiments, the antimicrobial compounds are provided in a pharmaceutical composition with a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, e.g., having an undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In certain embodiments, the compounds of the invention may be formulated for use as a bacteriocidal composition for use on surfaces that tend to serve as a support for biofilms, e.g., catheters. The bacteriocidal compositions include the compound and, for example, a suitable carrier. The bacteriocidal compositions may be provided in a form comprising the II-HMGR inhibitor in a concentration effective to kill or inhibit the growth of bacteria, or conveniently may be supplied in a concentrated form to be diluted prior to use.

The following non-limiting examples are intended to be purely illustrative.

EXAMPLES

Chemistry—General. All biologically tested compounds produced HPLC traces in which the major peak accounted for ≥95% of the combined total peak area when monitored by a UV detector at 254 nm. $^1$H NMR spectra were run at 300 MHz and $^{13}$C spectra were determined at 75.46 MHz in CDCl$_3$, DMSO-d$_6$, or CD$_3$OD. Chemical shifts are given in parts per million (ppm) on the delta (δ) scale. Chemical shifts were calibrated relative to those of the solvents.[1] Flash chromatography was performed on 230-400 mesh silica and preparative TLC separations utilized Analtech Uniplates with glass supported silica (20×20 cm, 2000 micron thickness) and UV indicator (254 nM). The progress of reactions was monitored with Baker-flex silica gel IB2-F plates (0.25 mm thickness). Mass spectra were recorded at 70 eV. High resolution mass spectra for all ionization techniques were obtained from a FinniganMAT XL95. Melting points were determined using capillary tubes with a Mel-Temp apparatus and are uncorrected. HPLC analyses were performed on Waters binary HPLC system (Model 1525, 20 μL injection loop) equipped with a Waters dual wavelength absorbance UV detector (Model 2487) set for 254 nm, and using a 5 μM C-18 reverse phase column. All reactions were conducted under argon or nitrogen atmosphere, unless otherwise specified. All yields reported refer to isolated yields.

Synthesis of thiazole compounds: In general, thiazole compounds were synthesized according to Schemes 1-4.

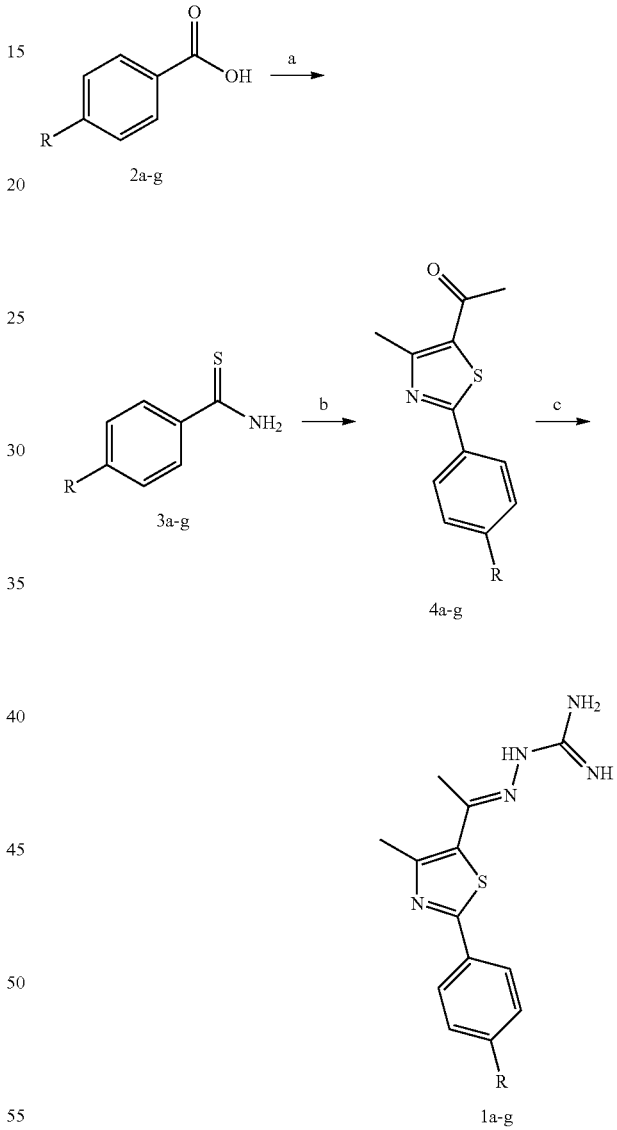

Scheme 1 a, R = CH$_2$(CH$_2$)$_2$CH$_3$
b, R = H
c, R = CH$_2$CH$_2$CH$_3$
d, R = CH$_2$(CH$_2$)$_3$CH$_3$
e, R = CH$_2$(CH$_2$)$_5$CH$_3$
f, R = CH$_2$(CH$_2$)$_7$CH$_3$
g, R = C(CH$_3$)$_3$ $^a$Reagents and conditions: a) i. SOCl$_2$, heat to reflux, 2 h, ii. NH$_4$OH, 0°-23° C., 2-5 h, Lawesson's reagent, dry THF, 50-60° C., 5-24 h; b) absolute ethanol, α-chloroacetylacetate, heat to reflux, 12 H, 63%; c) aminoguanidine hydrochloride, absolute ethanole, heat to reflux, 24 h.

Thiazole methylketone derivatives 4a-g were prepared in moderate yields by heating thioamides 3a-g, obtained by treatment of the corresponding amides with Lawesson's reagent in dry THF, with 3-chloropentane-2,4-dione in absolute ethanol (Scheme 1). The methyl ketones 4a-g were gently heated with aminoguanidine hydrochloride in the presence of lithium chloride as a catalyst to afford hydrazinecarboximidamide derivatives 1a-g (Scheme 1). Similarly, compound 1h was obtained from its corresponding methyl ketone 4h (Scheme 2).

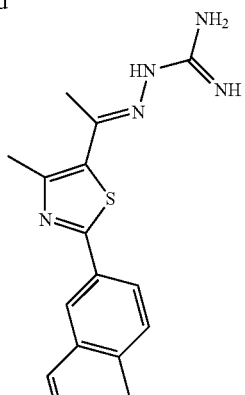

1h

[a]Reagents and conditions: a) absolute ethanol, α-chloroacetate, heat to reflux, 12 h, 67%; b) aminoguanidine hydrochloride, absolute ethanole, heat to reflux, 24 h, 40%.

To prepare the cyclohexyl derivative 7 and its corresponding unsaturated analogue 8, Scheme 3 was adopted. 4-Iodo-phenylthiazole 4i was prepared in a similar way like other methyl ketones 4a-g described in Scheme 1, Coupling with cyclohexene was achieved via Heck's reaction using palladium acetate, triethylamine as a base, and DMF as a solvent (Scheme 3). So far, the cyclohexenyl ketone 5 was obtained in around 40% yield. Catalytical hydrogenation of 5 afforded the cyclohexyl ketone 6 in a quantitative yield (Scheme 3). Treatment of ketones 5 and 6 with aminoguanidine hydrochloride in the presence of catalytical amount of lithium chloride gave hydrazinecarboximidamide derivatives 7 and 8 as shown in Scheme 3.

Scheme 2

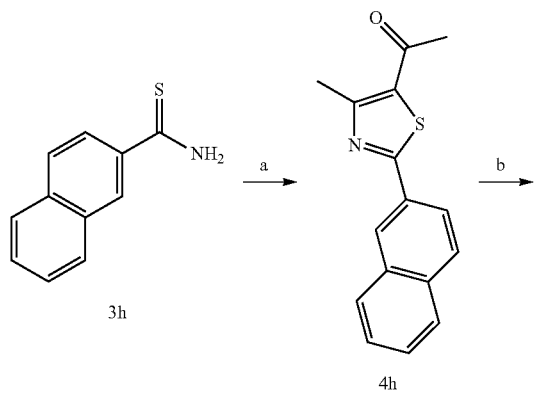

Scheme 3

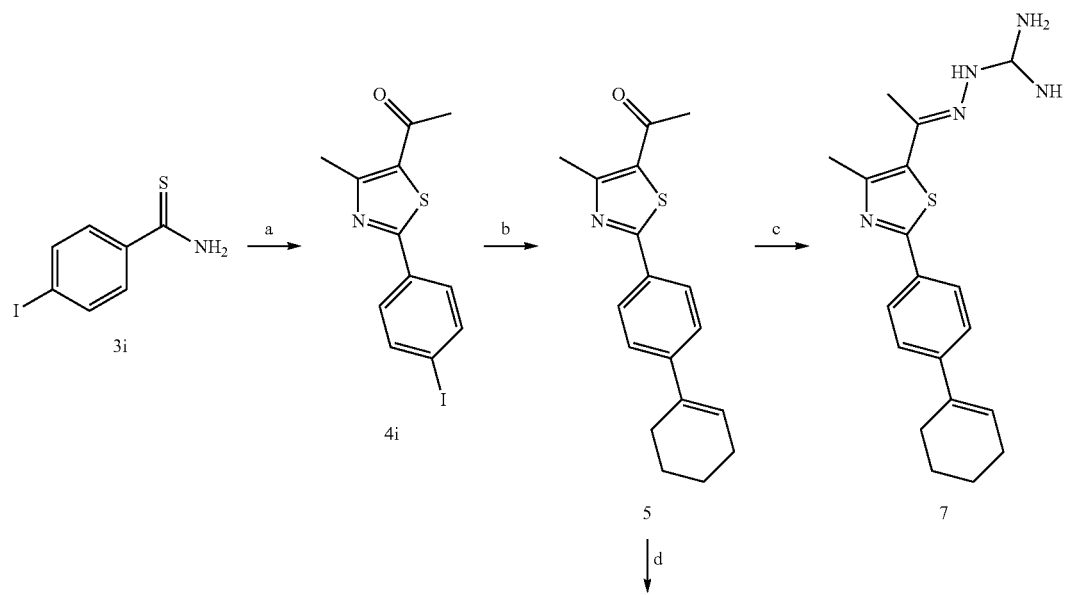

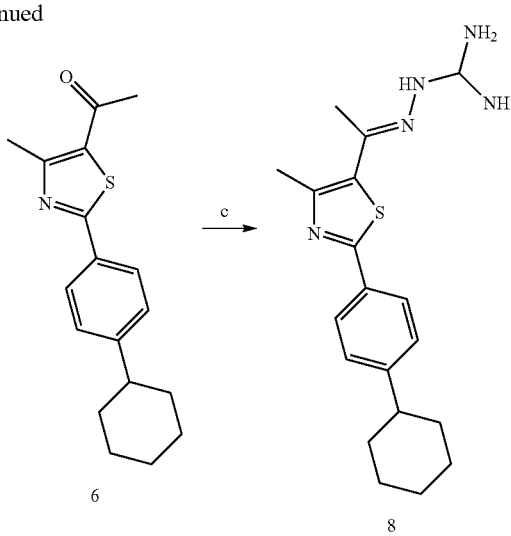

6 → 8

*Reagents and conditions: a) absolute ethanol, α-chloroacetoacetate, heat to reflux, 12 h, 58%; b) cyclohexene, PdAcO₂, Et₃N, DMF, 80 °C., 5 h, 39%; c) aminoguanidine hydrochloride, absolute ethanole, heat to reflux, 24 h; d) H₂, Pd/C, methanol, 23 °C., 24 h, 38-42%.

The biphenylthioamide derivative 10 was obtained from its corresponding commercially available aldehyde 9. First, the aldehyde 9 was converted into its corresponding amide using a method described by Chill and Mebane. Briefly, the aldehyde 9 was allowed to react with hydroxylamine hydrochloride in DMSO to form the corresponding nitrile analogue. Concentrated aqueous sodium hydroxide solution was added dropwise to the in situ formed nitrile, followed by careful and slow addition of hydrogen peroxide to afford the amide in a high yield. The crude amide was allowed to react with Lawesson's reagent in dry THF to afford the corresponding thioamide 10, which was treated with 3-chloro-2,4-pentanedione to give thiazole derivative 11 in moderate yield (Scheme 4). Treatment of 11 with aminoguanidine hydrochloride in the presence of a catalytic amount of lithium chloride gave the desired compound 12 as detailed before in the previous schemes.

Scheme 4

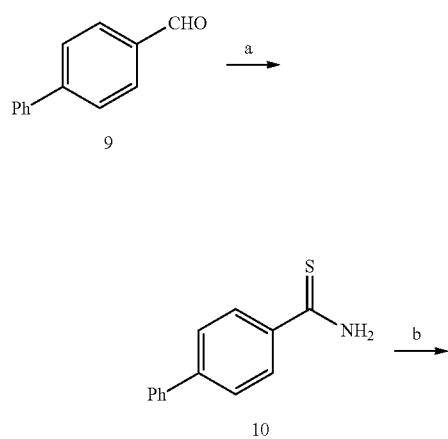

11 → 12

*Reagents and conditions: a) i. H₂NOH•HCl, DMSO, 100° C., 20 min; ii. NaOH, H₂O₂, 12 h; iii. Lawesson's reagent, THF, 23° C., 12 h; b) absolute ethanol, 3-chloropentane-2,4-dione, heat to reflux, 12 h, 49%; c) aminoguanidine hydrochloride, absolute ethanole, heat to reflux, 24 h, 45%

Preparation of Thioamides 3a-g. General Procedure. Amides 3a-g (1-5 mmol), which were obtained by treatment of their corresponding carboxylic acids 2a-g with thionyl chloride followed by gradual and addition to ammonia solution, and Lawesson's reagent (1.2 equiv.) were added to dry THF (15-40 mL). The reactions mixtures were stirred at room temperature for 5-12 h. The solvent was evaporated under reduced pressure and the residues were partitioned between aqueous NaHCO₃ (2 M, 25-50 mL) and ethyl acetate (25-75 mL). The organic solvent was separated and dried over anhydrous MgSO₄. The crude products were further purified by silica gel flash chromatography, using hexane-ethyl acetate (4:1), to yield the corresponding thioamides as yellow solids (55-57%). 4-n-Butylbenzamide, butylthiobenzamide (3a), thiobenzamide (3b), 4-n-propylbenzamide, propylthiobenzamide (3c), 4-n-pentylbenzamide, pentylthiobenzamide (3d), 4-n-heptylbenzamide (2e), 4-n-heptylthiobenzamide (3e), 4-nonylbenzamide, 4-t-butylbenzamide, 4-t-butylthiobenzamide (3g) are reported.

4-Nonylthiobenzamide (3f). Yellow solid (550 mg, 76%): mp 57° C. $^1$H NMR (DMSO-d$_6$) δ 9.76 (brs, 1 H), 9.39 (brs, 1 H), 7.82 (d, J=8.1 Hz, 2 H), 7.21 (d, J=8.1 Hz, 2 H), 2.58 (t, J=7.5 Hz, 2 H), 1.55 (m, 2 H), 1.25 (m, 12 H), 0.83 (t, J=6.9 Hz, 3 H); $^{13}$C NMR (DMSO-d$_6$) δ 200.65, 146.95, 137.71, 128.66, 128.32, 35.78, 32.20, 31.61, 29.88, 29.78, 29.62, 29.56, 23.02, 14.88; ESIMS m/z (rel intensity) 264 (MH$^+$, 100); HREISMS, m/z 264.1784 MH$^+$, calcd for C$_{16}$H$_{26}$NS 264.1786.

Preparation of Methyl Ketones 4a-i. General Procedure. Thiobenzamides 3a-i (2-10 mmol) and 3-chloropentane-2,4-dione (1.4 equiv.) were added to absolute ethanol (10-30 mL). The reaction mixtures were heated at reflux for 12-24 h. After evaporation of solvent under reduced pressure, the brown residues were collected and purified by silica gel flash chromatography, using hexane-ethyl acetate (9:1), to yield the desired compounds. Compounds 4a and 4b are previously reported. The physical properties and characterization data of 4c-i are listed below 1-[4-Methyl-2-(4-propylphenyl)thiazol-5-yl]ethanone (4c). White solid (135 mg, 61%): mp 57° C. $^1$H NMR (CDCl$_3$) δ 8.10 (d, J=9.0 Hz, 2 H), 7.32 (d, J=9.0 Hz, 2 H), 2.93 (s, 3 H), 2.6 (m, 5 H), 1.67 (m, 2 H), 0.96 (t, J=6.3 Hz, 3 H); $^{13}$C NMR (CDCl$_3$) δ 189.43, 171.04, 155.41, 148.87, 131.59, 129.63, 127.87, 126.96, 38.00, 30.36, 24.06, 16.88, 13.67; CIMS m/z (rel intensity) 260 (MH$^+$, 100); HRMS (EI), m/z 259.1033 M$^+$, calcd for C$_{15}$H$_{17}$NOS 259.1031.

1-[4-Methyl-2-(4-pentylphenyl)thiazol-5-yl]ethanone (4d). Colorless oil (159 mg, 76%). $^1$H NMR (CDCl$_3$) δ 7.85 (d, J=8.7 Hz, 2 H), 7.22 (d, J=8.7 Hz, 2 H), 2.73 (s, 3 H), 2.60 (t, J=6.0 Hz, 2 H), 2.50 (s, 3 H), 1.63 (m, 2 H), 1.33 (m, 4 H), 0.87 (t, J=6.0 Hz, 3 H); $^{13}$C NMR (CDCl$_3$) δ 190.33, 169.56, 159.39, 146.64, 130.71, 130.25, 129.04, 126.77, 35.79, 31.37; 30.79; 30.67; 22.45; 18.41; 13.97; CIMS m/z (rel intensity) 288 (MH$^+$, 100); HRMS (EI), m/z 287.1347 M$^+$, calcd for C$_{17}$H$_{21}$NOS 287.1344.

1-[4-Methyl-2-(4-hepylphenyl)thiazol-5-yl]ethanone (4e). Colorless oil (360 mg, 44%). $^1$H NMR (CDCl$_3$) δ 7.86 (d, J=8.1 Hz, 2 H), 7.25 (d, J=8.1 Hz, 2 H), 2.76 (s, 3 H), 2.63 (t, J=6.0 Hz, 2 H), 2.55 (s, 3 H), 1.62 (m, 2 H), 1.28 (m, 8 H), 0.87 (t, J=6.0 Hz, 3 H); $^{13}$C NMR (CDCl$_3$) δ 190.35, 169.64, 159.42, 146.70, 131.36, 130.73, 130.26, 129.06, 126.80, 35.84, 31.74, 31.13, 30.70, 29.16, 29.09, 22.60; 18.42; 14.05; CIMS m/z (rel intensity) 316 (MH$^+$, 100); HRMS (EI), m/z 315.1655 M$^+$, calcd for C$_{19}$H$_{25}$NOS 315.1657.

1-[4-Methyl-2-(4-nonylphenyl)thiazol-5-yl]ethanone (4f). Yellowish oil (450 mg, 60%). $^1$H NMR (CDCl$_3$) δ 7.87 (d, J=8.1 Hz, 2 H), 7.24 (d, J=8.1 Hz, 2 H), 2.77 (s, 3 H), 2.63 (t, J=7.0 Hz, 2 H), 2.55 (s, 3 H), 1.62 (m, 2 H), 1.29 (m, 12 H), 0.87 (t, J=6.9 Hz, 3 H); $^{13}$C NMR (CDCl$_3$) δ 190.42, 169.65, 159.44, 146.71, 130.75, 130.29, 129.07, 126.81; 35.86, 31.83, 31.14, 30.72, 29.48, 29.43, 29.25, 22.63, 18.45, 14.07; ESIMS m/z (rel intensity) 344 (MH$^+$, 100); HRESIMS, m/z 344.2052 M$^+$, calcd for C$_{21}$H$_{30}$NOS 344.2048.

1-{2-[4-(tert-Butyl)phenyl]-4-methylthiazol-5-yl}ethanone (4g). White solid (557 mg, 62%): mp 53° C. $^1$H NMR (CDCl$_3$) δ 7.84 (d, J=8.4 Hz, 2 H), 7.43 (d, J=8.4 Hz, 2 H), 2.72 (s, 3 H), 2.49 (s, 3 H), 1.31 (s, 9 H); $^{13}$C NMR (CDCl$_3$) δ 190.27, 169.35, 159.36, 154.65, 130.70, 129.97, 126.57, 125.90, 34.85, 31.00, 30.62, 18.37; CIMS m/z (rel intensity) 274 (MH$^+$, 100); HRMS (EI), m/z 273.1182 M$^+$, calcd for C$_{16}$H$_{19}$NOS 273.1187.

1-[4-Methyl-2-(naphthalen-2-yl)thiazol-5-yl]ethanone (4h). White solid (110 mg, 67%): mp 109° C. $^1$H NMR (CDCl$_3$) δ 8.41 (d, J=0.9 Hz, 1 H), 7.94 (d, J=1.8 Hz, 1 H), 7.84 (m, 3 H), 7.50 (d, J=9.0 Hz, 2 H), 2.76 (s, 3 H), 2.51(s, 3 H); $^{13}$C NMR (CDCl$_3$) δ 190.31, 169.28, 159.49, 134.50, 132.98, 131.21, 129.94, 128.79, 127.80, 127.54, 126.93, 126.67, 123.71, 30.69, 18.45; ESIMS m/z (rel intensity) 268 (MH$^+$, 100); HRESIMS, m/z 268.0793 MH$^+$, calcd for C$_{16}$H$_{14}$NOS 264.0796.

1-[2-(4-Iodophenyl)-4-methylthiazol-5-yl]ethanone (4i). Brownish solid (1050 mg, 58%): mp 123° C. $^1$H NMR (CDCl$_3$) δ 7.80 (d, J=8.7 Hz, 2 H), 7.68 (d, J=8.7 Hz, 2 H), 2.76 (s, 3 H), 2.56 (s, 3 H); $^{13}$C NMR (CDCl$_3$) δ 190,29, 168.05, 159.44, 138.14, 132.11, 131.43, 128.13, 97.66, 30.70, 18.36; CIMS m/z (rel intensity) 344 (MH$^+$, 100); HRMS (EI), m/z 342.9535 M$^+$, calcd for C$_{12}$H$_{10}$INOS 342.9528.

Preparation of 1-{2-[4-(1-Cyclohexenyl)phenyl]-4-methylthiazol-5-yl}ethanone (5). A solution of 4-iodophenylthiazole 4i (100 mg, 0.3 mmol) in dry DMF (5 mL) was charged with Pd(OAc)$_2$ (5 mg), cyclohexene (1 mL) and triethylamine (0.5 mL). The reaction mixture was heated at 80° C. for 5 h. The reaction mixture was quenched with distilled water (10 mL) and extracted with ethyl acetate (30 mL). The organic layer was separated and dried over anhydrous Na$_2$SO$_4$. After evaporation of solvent under reduced pressure, the oily residue was collected and purified by silica gel flash chromatography, using hexane-ethyl acetate (9:1), to yield faint yellowish oil (35 mg, 39%). $^1$H NMR (CDCl$_3$) δ 7.90 (d, J=8.1 Hz, 2 H), 7.29 (d, J=8.1 Hz, 2 H), 5.76 (m, 2 H), 2.80 (m, 1 H), 2.77 (s, 3 H), 2.55 (s, 3 H), 2.27-1.24 (m, 6 H); $^{13}$C NMR (CDCl$_3$) δ 190.45, 169.54, 159.46, 150.94, 130.84, 130.63, 128.42, 127.60, 126.97, 126.33, 40.06, 32.98, 30.73, 29.40, 25.59, 18.45; CIMS m/z (rel intensity) 298 (MH$^+$, 100); HRMS (EI), m/z 297.1189 M$^+$, calcd for C$_{18}$H$_{19}$NOS 297.1187.

1-[2-(4-Cyclohexylphenyl)-4-methylthiazol-5-yl]ethanone (6). Compound 5 (100 mg, 0.3 mmol) and Pd (50 mg, 10% on activated charcoal) were added to deoxygenated absolute methanol (10 mL). The hydrogen was applied via a balloon. The reaction mixture was stirred at room temperature for 24 h, and then filtered through celite. The filtrate was collected and the solvent was evaporated under reduced pressure to yield compound 7 as a colorless oil (100 mg, 100%). $^1$H NMR (CDCl$_3$) δ 7.87 (d, J=8.4 Hz, 2 H), 7.27 (d, J=8.4 Hz, 2 H), 2.75 (s, 3 H), 2.53 (s, 3 H), 2.51 (m, 1 H), 1.85-1.73 (m, 5 H), 1.43-1.24 (m, 5 H); $^{13}$C NMR (CDCl$_3$) δ 190.45, 169.65, 159.44, 151.70, 130.74, 130.40, 127.51, 126.88, 44.50, 34.10, 30.70, 26.69, 25.99, 18.44; CIMS m/z (rel intensity) 300 (MH$^+$, 100); HRMS (EI), m/z 299.1350 M$^+$, calcd for C$_{18}$H$_{21}$NOS 299.1344.

Preparation of 1-(2-([1,1'-Biphenyl]-4-yl)-4-methylthiazol-5-yl)ethanone (11). The aldehyde 9 (800 mg, 5.2 mmol) was added to a solution of hydroxylamine hydrochloride (725, 10.5 mmol) in DMSO (10 mL), and the reaction mixture was stirred at 100° C. for 20 min. The heater was turned off and aqueous NaOH solution (600 mg dissolved in 5 mL distilled water) was slowly added to the reaction mixture over a 2 min period with stirring, and then hydrogen peroxide 50% (5 mL) was slowly and carefully added over a 10 min period. The reaction mixture was further stirred for 12 h and extracted with ethyl acetate (3×10 mL), dried over anhydrous Na$_2$SO$_4$, and evaporated under reduced pressure to afford the corresponding amide as a white solid. The crude amide (2 mmol) and Lawesson's reagent (980 mg, 2.4 mmol) were added to dry THF (15 mL). The reaction mixture was stirred at room temperature for 12 h. The solvent was evaporated under reduced pressure and the residue was partitioned between aq NaHCO$_3$ (25 mL) and ethyl acetate (25 mL). The organic solvent was separated and dried over anhydrous Na$_2$SO$_4$. The crude product was further purified by silica gel flash chromatography, using hexane-ethyl acetate (4:1), to yield the corresponding thioamide 10 as a yellow solid. The obtained thioamide 10 (215 mg, 1 mmol) and chloroacetoacetate (0.3 mL, 2.5 mmol) were added to absolute ethanol (10 mL). The reaction mixture was heated at reflux for 24 h. After evaporation of solvent under reduced pressure, the oily residue was collected and purified by silica gel flash chromatography, using hexane-ethyl acetate (9:1), to yield compound 11 as an off-white solid (290 mg, 49%): mp 124-125° C. $^1$H NMR (CDCl$_3$) δ 8.36 (d, J=8.4 Hz, 2 H), 7.77 (d, J=8.4 Hz, 2 H), 7.64 (d, J=8.7 Hz, 2 H), 7.46 (m, 3 H), 3.03, 2.64; $^{13}$C NMR (CD$_3$OD) δ 190.45, 153.24, 148.20, 143,78, 140.00, 130.51, 130.28, 128.49, 127.94, 127.14, 126.14, 126.01, 23.90, 17.99; ESIMS m/z (rel intensity) 290 (MH$^+$, 100); HRESIMS, m/z 290.1039 MH$^+$, calcd for C$_{18}$H$_{27}$NS 290.1939.

Preparation of Hydrazinecarboximidamides 1a-h, 7, 8, and 12. General Procedure. The ketone derivatives 3a-h, 5, 6, 11 or 16 (1-10 mmol) were dissolved in absolute ethanol (10-50 mL). Aminoguanidine hydrochloride (1 equiv.) and a catalytic amount of LiCl (5-20 mg) were added. The reaction mixtures were heated at reflux for 24 h. The solvent was evaporated under reduced pressure. The crude product was purified by crystallization from 70% methanol, and then recrystallized from absolute methanol to afford the desired compounds as solids. Compound 1a was previously reported (Mayhoub AS et al. *Bioorgan Med Chem* 2011; 19: 3845-54). The physical properties and characterization data of 1b-h, 7, 8, and 11 are listed below:

2-[1-(4-Methyl-2-phenylthiazol-5-yl)ethylidene]hydrazinecarboximidamide (1b). Yellowish white solid (124 mg, 61%): mp 195-196° C. $^1$H NMR (DMSO-d$_6$) δ 11.65 (brs, 1 H), 8.88 (brs, 1 H), 7.91-7.88 (m, 4 H), 7.48 (m, 3 H) 2.60 (5, 3 H), 2.43 (s, 3 H); $^{13}$C NMR (DMSO-d$_6$) δ 165.79, 160.11, 156.96, 153.33, 147.96, 133.51, 131.53, 130.24, 126.90, 19.27, 1903; ESIMS m/z (rel intensity) 274 (MH$^+$, 100); HRESIMS, m/z 274.1128 MH$^+$, calcd for C$_{13}$H$_{16}$N$_5$S 274.1126; HPLC purity (methanol:water, 1:1): 95.44%.

2-{1-[4-Methyl-2-(4-propylphenyl)thiazol-5-yl]ethylidene}hydrazinecarboximid-amide (1c). Yellowish white solid (100 mg, 55%): mp 256-257° C. $^1$H NMR (DMSO-d$_6$) δ 11.47 (brs, 1 H), 7.80 (d, J=8.1 Hz, 2 H). 7.76 (brs, 3 H), 7.29 (d, J=8.1 Hz, 2 H). 2.58 (s, 3 H), 2.55 (t, J=7.8 Hz, 2 H), 2.41 (s, 3 H), 1.60 (m, 2 H), 0.88 (t, J=7.5 Hz, 3 H); $^{13}$C NMR (DMSO-d$_6$) δ 165.01, 156.80, 153.28, 148.14, 146.06, 131.21, 130.14, 126.95, 126.88, 37.94, 24.71, 19.14, 19.05, 14.54; ESIMS m/z (rel intensity) 316 (MH$^+$, 100); HRESIMS, m/z 316.1590 MH$^+$, calcd for C$_{16}$H$_{22}$N$_5$S 316.1596; HPLC purity (methanol:water, 1:1): 97.09

2-{1-[4-Methyl-2-(4-pentylphenyl)thiazol-5-yl]ethylidenehydrazinecarboximid-amide (1d). Yellow solid (54 mg, 50%); mp 210° C. $^1$H NMR (DMSO-d$_6$) δ 11.41 (brs, 1 H), 7.81 (d, J=7.8 Hz, 2 H), 7.78 (brs, 3 H), 7.31 (d, J=7.8 Hz, 2 H), 2.62 (m, 5 H), 2.41 (s, 3 H), 1.57 (m, 2 H), 1.27 (m, 4 H), 0.84 (t, J=7.5 Hz, 3 H); $^{13}$C NMR (DMSO-d$_6$) δ 165.43, 156.16, 152.71, 147.59, 145.73, 130.57, 130.47, 129.51, 126.49, 35.25, 31.21, 30.66, 22.26, 18.52, 18.45, 14.24; ESIMS m/z (rel intensity) 344 (MH$^+$, 100); HRESIMS, m/z 344.1913 MH$^+$, calcd for C$_{18}$H$_{26}$N$_5$S 244.1909; HPLC purity (methanol:water, 1:1): 95.12%.

2-{1-[4-Methyl-2-(4-heptylphenyl)thiazol-5-yl]ethylidenehydrazinecarboximid-amide (1e). Yellow solid (151 mg, 53%): mp 233-235° C. $^1$H NMR (DMSO-d$_6$) δ 11.43 (brs, 1 H), 7.80 (m, 5 H), 7.30 (d, J=8.1 Hz, 2 H), 2.61 (m, 5 H), 2.42 (s, 3 H), 1.55 (t, 2 H), 1.24 (m, 8 H), 0.82 (t, J=6.6 Hz, 3 H); $^{13}$C NMR (DMSO-d$_6$) δ 165.98, 156.86, 153.25, 148.09, 146.28, 131.17, 131.06, 130.07, 126.89, 35.88, 32.15, 31.57, 29.54, 29.43, 23.00, 19.19, 19.05, 14.86; ESIMS m/z (rel intensity) 372 (MH$^+$, 100); HRESIMS, m/z 372.2228 MH$^+$, calcd for C$_{20}$H$_{30}$N$_5$S 372.2222; HPLC purity (methanol:water, 1:1): 99.31%.

2-{1-[4-Methyl-2-(4-nonylphenyl)thiazol-5-yl]ethylidenehydrazinecarboximid-amide (1f). Yellow solid (133 mg, 55%): mp 203-206° C. $^1$H NMR (DMSO-d$_6$) δ 11.32 (brs, 1 H), 7.79 (d, J=8.1 Hz, 2 H), 7.60 (brs, 3 H), 7.28 (d, J=8.1 Hz, 2 H), 2.58 (m, 5 H), 2.41 (s, 3 H), 1.55 (m, 2 H), 1.22 (m, 12 H), 0.82 (t, J=6.9 Hz, 3 H); $^{13}$C NMR (DMSO-d$_6$) δ 165.80, 156.87, 153.45, 147.99, 146.28, 131.19, 131.60, 129.44, 126.25, 36.34, 35.29, 31.60, 30.98, 29.28, 29.19, 28.99, 22.42, 18.46, 18.39, 14.27; ESIMS m/z (rel intensity) 400 (MH$^+$, 100); HRESIMS, m/z 400.2540 MH$^+$, calcd for C$_{22}$H$_{34}$N$_5$S 400.2535; HPLC purity (methanol:water, 1:1): 95.40%.

2-{1-[2-(4-(tert-Butyl)phenyl)-4-methylthiazol-5-yl]ethylidene}hydrazinecarboximid-amide (1g). Off-white solid (155 mg, 67%): nip 252-253° C. $^1$H NMR (DMSO-d$_6$) δ 11.41 (brs, 1 H), 7.83 (d, J=8.4 Hz, 2 H), 7.65 (brs, 3 H), 7.51 (d, J=8.4 Hz, 2 H), 2.59 (s, 3 H), 2.41 (s, 3 H), 1.29 (s, 9 H); $^{13}$C NMR (DMSO-d$_6$) δ 165.90, 156.75, 154.40, 153.34, 148.22, 131.09, 130.94, 127.02, 126.76, 35.60, 31.81, 19.13, 19.05; ESIMS m/z (rel intensity) 330 (MH$^+$, 100); HRESIMS, m/z 330.1755 MH$^+$, calcd for C$_{17}$H$_{24}$N$_5$S 330.1752; HPLC purity (methanol:water, 1:1): 96.86%.

2-{1-[4-Methyl-2-(naphthalen-2-yl)thiazol-5-yl]ethylidene}hydrazinecarboximid-amide (1h). Yellow solid (80 mg, 40%): mp 288-290° C. $^1$H NMR (DMSO-d$_6$) δ 11.39 (brs, 1 H), 8.50 (s, 1 H), 8.08-7.94 (m, 4 H), 7.73 (brs, 3 H), 7.58 (m, 2 H), 2.64 (s, 3 H), 2.44 (s, 3 H); $^{13}$C NMR (DMSO-d$_6$) δ 165.86, 156.73, 153.56, 148.19, 134.70, 133.75, 131.77, 130.94, 129.91, 129.59, 128.71, 128.41, 128.07, 126.44, 124.20, 19.06, 17.18; ESIMS m/z (rel intensity) 324 (MH$^+$, 100); HRESIMS, m/z 324.1179 MH$^+$, calcd for C$_{17}$H$_{18}$N$_5$S 324.1283; HPLC purity (methanol:water, 1:1): 95.99%.

2-{1-[2-(4-(1-Cyclohexenyl)phenyl)-4-methylthiazol-5-yl]ethylidene}hydrazine-carboximidamide (7). Yellow solid (58 mg, 42%): mp 213-215° C. $^1$H NMR (DMSO-d$_6$) δ 11.29 (brs, 1 H), 7.82 (d, J=8.1 Hz, 2 H), 7.37 (d, J=8.1 Hz, 2 H), 7.05 (brs, 3 H), 5.74 (m, 2 H), 2.80 (m, 1 H), 2.58 (s, 3 H), 2.37 (s, 3 H), 2.20-2.06 (m, 3 H), 1.82-1.71 (m, 3 H); $^{13}$C NMR (DMSO-d$_6$) δ 164.46, 157.32, 151.22, 149.83, 146.15, 132.04, 131.07, 128.02, 127,11, 126.79, 126.31, 42.01, 32.85, 29.43, 25.59, 18.49, 17.77; ESIMS m/z (rel intensity) 354 (MH$^+$, 100); HRESIMS, m/z 354.1759 MH$^+$, calcd for C$_{19}$H$_{24}$N$_5$S 354.1752; HPLC purity (methanol:water, 1:1): 97.50%.

2-{1-[2-(4-Cyclohexylphenyl)-4-methylthiazol-5-yl]ethylidene}hydrazinecarboximid-amide (8). Yellow solid (42 mg, 38%): mp 273-276° C. $^1$H NMR (DMSO-d$_6$) δ 11.27 (brs, 1 H), 7.80 (d, J=8.4 Hz, 2 H), 7.50 (brs, 3 H), 7.33 (d, J=8.4 Hz, 2 H), 2.58 (s, 3 H), 2.57 (m, 1 H), 2.40 (s, 3 H), 1.76 (m, 5 H), 1.37 (m, 4 H); $^{13}$C NMR (DMSO-d$_6$) δ 166.88, 156.35, 152.19, 150.97, 147.98, 130.33, 130.20, 127.13, 126.04, 44.34, 33.86, 26.35; 25.62, 16.70, 16.20; ESIMS m/z (rel intensity) 356 (MH$^+$; 100); HRESIMS, m/z 356.1912 MH$^+$, calcd for C$_{19}$H$_{26}$N$_5$S 356.1909; HPLC purity (methanol:water, 1:1): 98.09%.

2-{1-[2-([1,1'-Biphenyl]-4-yl)-4-methylthiazol-5-yl]ethylidene}hydrazinecarboximid-amide (12). Yellow solid (104 mg, 45%): mp 278-280° C. $^1$H NMR (CD$_3$OD) δ 8.00 (d, J=9.0 Hz, 2 H), 7.73 (d, J=9.0 Hz, 2 H), 7.66 (d, J=9.0 Hz, 2 H), (d, J=9.0 Hz, 2 H), 7.36 (t, J=9.0 Hz, 2 H), 2.66 (s, 3 H), 2.42 (s, 3 H); $^{13}$C NMR (CD$_3$OD) δ 166.40, 155.92, 152.80, 148.24, 143.22, 139.60, 131.49, 130.29, 128.59, 127.16, 127.04, 126.47, 126.34, 16.74, 16.26; ESIMS m/z (rel intensity) 350 (MH$^+$, 100); HRESIMS, m/z 350.1435 MH$^+$, calcd for C$_{19}$H$_{20}$N$_5$S 350.1439; HPLC purity (methanol:water, 1:1): 95.96%.

Bacterial strains, reagents, and antibiotic. A list and description of bacterial strains presented in this study is provided in Table 1 as shown in FIG. 6. MRSA clinical isolates, vancomycin intermediate *Staphylococcus aureus* (VISA), vancomycin resistant *Staphylococcus aureus* (VRSA) and linezolid-resistant strains were obtained through the Network of Antimicrobial Resistance in *Staphylococcus aureus* (NARSA) program. In addition, MRSA ATCC 43300 was obtained from the American Type Cultural Collection (Manassas, Va., USA). Lysostaphin (Sigma-Aldrich, St. Louis, Mo, USA) at 20 μg/mL was prepared in 50 mM Tris-HCl (pH 8.00) (Sigma-Aldrich, St. Louis, Mo., USA). Vancomycin hydrochloride powder was purchased commercially (Gold Biotechnology Inc., St, Louis, Mo., USA) and dissolved in dimethyl sulfoxide (DMSO) (Sigma-Aldrich, St. Louis, Mo., USA).

Determination of minimum inhibitory concentration (MIC). The MICs of the lead thiazole compound (compound 1a) and nine derivatives tested against all 18 MRSA strains were determined, in triplicate samples, using the broth microdilution method in accordance with the recommendations contained in the MI guidelines. The MIC was categorized as the concentration at which no visible growth of bacteria was observed in a particular well.

Time-kill assay. MRSA (USA300) cells, in the logarithmic growth phase, were diluted to 1.0×10$^6$ colony-forming units (CFU/mL) and exposed to concentrations equivalent to 3.0×MIC (in triplicate) of compounds 1a, 1d, 8, and vancomycin in trypticase soy broth (TSB) (Becton, Dickinson and Company, Sparks, Md., USA). Viable CFU/mL was determined by serial dilution and plating on trypticase soy agar (TSA) (Becton, Dickinson and Company, Sparks, Md., USA) plates after 0, 2, 4, 6, 8, 10, and 12 hours of incubation at 37 ° C. to identify the time required to reduce the bacterial cell count by 3-log$_{10}$.

In vitro cytotoxicity analysis: Compounds were assayed at concentrations of 2 μM, 4 μM, 8 μM, and 16 μM against a macrophage cell line (J774.A1) to determine the potential toxic effect in vitro, Murine macrophage cells were cultured in Dulbeco's Modified Eagle Medium (Sigma-Aldrich, St. Louis, Mo., USA) with 10% Fetal Bovine Serum (USA Scientific, Inc.) at 37° C. with 5% CO$_2$. Controls received DMSO alone at a concentration equal to that in drug-treated cell samples. The cells were incubated with the compounds in a 96-Well Plate at 37° C. and 5.0% CO$_2$ for 24 hours prior to addition of the assay reagent MTS 3-(4,5-dimethylthiazol-2-yl)-5-(3-carboxymethoxyphenyl)-2-(4-sulfophenyl)-2H-tetrazolium) (Promega, Madison, Wis., USA). The reagent measures the succinate dehydrogenase mitochondrial activity as an indicator of cell viability and proliferation. Corrected absorbance readings (actual absorbance readings for each treatment subtracted from background absorbance) were taken using a kinetic ELISA microplate reader (Molecular Devices, Sunnyvale, Calif., USA). The quantity of viable cells after treatment with each compound was expressed as a percentage of the control, DMSO.

Calculation of partition coefficient (log P) and topological polar surface area (TPSA). Calculated log P and TPSA values for the thiazole compounds were obtained using MIinspiration Cheminformatics software available on the internet (http://www.molinspiration.com/).

Loss of 260 and 280-nm cellular absorbing material: In order to investigate the antimicrobial effect of the lead compound on the integrity of the bacterial cell membrane, the release of 260 and 280 nm absorbing components was determined spectrophotometrically after bacterial incubation with the lead compound. The cell suspension of 1.0×10$^9$ CFU/mL MRSA was incubated with 4.0×MIC of the lead compound at 37° C. for 30 minutes. For the release of 260 and 280 nm absorbing material, the bacterial suspension (control) was treated with lysostaphin for 30 minutes. The absorbance of cell supernatant at 260 and 280 nm was determined using a spectrophotometer (Jenway 6305). The average OD$_{260}$ and OD280 values of triplicates of each treatment option were calculated and expressed as the proportion of average OD$_{260}$ (or OD$_{280}$) for each treatment option compared to the average OD$_{260}$ (or OD$_{280}$) for the positive control (lysostaphin).

Flow cytometry and LIVE/DEAD® Fixable Dead Cell Stain: The action of the lead compound on cell membrane permeability of MRSA was assayed using the LIVE/DEAD® Fixable Dead Cell Stain Kit (Invitrogen, Eugene, Oreg., USA) according to the manufacturer's instructions. 1.0×10$^9$ CFU/mL MRSA ATCC 43300 cells were incubated with either 4.0×MIC of the lead thiazole compound, lysostaphin (the positive control), or DMSO (negative control) for 10 minutes at 37° C. with shaking. Post-treatment cells were fixed with 3.7% formaldehyde; the cells were then screened with a Beckman Coulter FC500 flow cytometer. The data were analyzed using FlowJo software to determine the ratio of intact (cells which did not take-up the dye) to compromised (cells which did take-up the dye) cells post-treatment.

Molecular target/mechanism of resistance identification through genomic insertion of transposon with a strong outward-oriented promoter. Overexpression of the target/resistance mechanism was carried out using a transposon with a strong outward-oriented promoter for the random overexpression of neighboring genes in *Bacillus subtilis*. The pEP26 delivery vector carrying the transposon with the promoter (TnHyJump) was transformed into *B. subtilis* using known methods. For transposon integration into the bacterial DNA, cells were grown for 10 hours at 25° C., serially diluted, subcultured in dual selection TSA plates containing 5 μg/ml chloramphenicol (for selection of transposon) and 3.0×MIC compound 1a (for selection of compound resistance) and incubated overnight at 42° C. Growth at 42° C. is nonpermissive for the maintenance of the delivery vector, and thus chloramphenicol/compound 1a resistance primarily arises from the chromosomal insertion of the transposon. 12 colonies out of 142 colonies on 3.0×MIC compound 1a were screened for MIC shift (resistance) against compound 1a using the broth microdilution method to confirm for resistance. Genomic DNA was extracted from resistant colonies (recombinants that were capable of growth at concentrations that were inhibitory to the control) and were sent for sequencing. Insertion sites were identified by sequencing. Transposon location within the resistant B. subtilis genome, orientation and flanking genes were determined by performing a BLASTN search on the NCBI public BLAST server.

Statistical analysis: All statistical analyses were performed using the Student two-tailed t test using Microsoft EXCEL, with the exception of the cytotoxicity data. An ANOVA table (using the Tukey's HSD test) was constructed for the cytotoxicity data using KaleidaGraph. P values ≤0.01 for all statistical tests performed were considered significant.

Results

As disclosed herein, ten newly synthesized thiazole compounds were discovered to be potent antimicrobial agents against 18 tested multi drug-resistant strains of S. aureus. These compounds were shown to rapidly eliminate MRSA growth within a six-hour window. The tested thiazole compounds have only limited toxicity to murine macrophage cells. Further, these compounds have favorable clog P and TPSA values, which are expected to correlate with good solubility and permeability characteristics. Finally, the thiazole compounds do not act by disrupting the physical integrity of either the bacterial cell wall or cytoplasmic membrane.

Antimicrobial activity of novel synthetic thiazole compounds against MRSA and VRSA. Turnig to FIG. 7A-C, Table 2 shows the chemical structure of the lead compound and nine synthesized derivatives and the MIC values against bacterial strains determined using the broth microdilution technique. The ten tested substituted thiazole compounds inhibited growth of 18 different strains of MRSA and VRSA at a concentration ranging from 0.4-5.5 µg/mL. The lead compound 1a was found to inhibit the growth of MRSA strains at concentrations ranging from 1.4-5.5 µg/mL. Subsequently synthesized derivatives demonstrated a two- to five-fold improvement in the MIC values, Initially, the effect of increasing the length of the alkyl side chain, through insertion of methylene units, was explored. As the length of the alkyl side chain increased from two (compound 1c) to three (compound 1a) to four (compound 1d) methylene units, there was a consistent improvement in the MIC values observed against all MRSA strains tested. However, additional lengthening of the alkyl side chain appeared to nullify the improvement observed in the antimicrobial activity, as the MIC for compound 1e (containing six methylene units) nearly matched or exceeded the values obtained for compound 1d. This result held true as an increase to eight methylene units (compound 1f) resulted in an MIC value that nearly matched or exceeded the MIC value attained for compound 1a. Altogether this indicates that an alkyl side chain with four methylene units exhibits the optimum potency against MRSA and addition of methylene units to the alkyl side beyond four units will not significantly enhance the antimicrobial activity of the lead compound.

Replacement of the linear alkyl side chain with a branched alkane (compound 1g) produced mixed results. There was a modest improvement in the MIC values against six MRSA strains (1.0 µg/mL for compound 1g compared to 1.4 µg/mL for compound 1a) and a nearly two- to five-fold enhancement in the MIC for five additional strains. Further modifications using branched alkanes or alkenes would be useful to explore in order to determine if a consistent reduction in the MIC value against all MRSA strains tested can be attained. Substitution of the alkyl side chain with a fused to ring system (compound 1h) did not significantly enhance the activity of the derivative against the MRSA strains tested, with the exception of VRSA (a near three-fold reduction in MIC was observed compared to 1a). However, replacement of the alkyl side chain with conformationally restricted analogues (compounds 7, 8, and 12) demonstrated the most consistent, significant improvement in the MIC value obtained relative to the lead compound (two- to four-fold improvement against 16 MRSA strains tested).

The MIC values obtained for compounds 7, 8, and 12 on multiple occasions matched or were lower than the antibiotic vancomycin against the MRSA strains tested. Furthermore, all ten thiazole compounds proved to be more potent than vancomycin in inhibiting growth of VISA cells against three strains (VISA ATCC 700699, VISA HIP07256, VISA LIM 3) which possess intermediate sensitivity to glycopeptide antibiotics (such as vancomycin). In addition to this, the thiazole compounds proved effective against VRSA, a vancomycin-resistant strain, inhibiting growth at a range of 0.5 to 3.0 µg/mL (compared to vancomycin which had an MIC of 185.5 µg/mL). Compounds 7, 8, and 12 also proved more effective at eliminating growth of MRSA NRS119, a strain resistant to linezolid (a drug of last resort in treatment of MRSA infections), and several strains resistant to multiple antibiotic classes including lincosamides, aminoglycosides, fluoroquinolones, and macrolides (USA100, USA200, and USA500). In addition to this, all 10 compounds exhibited excellent activity against MRSA USA300, a strain responsible for most cases of community-acquired MRSA (CA-MRSA) and MRSA skin and soft tissue infections (SSTIs) in the United States. These results indicate the potential these novel thiazole compounds may have in the future as alternative treatment options for MRSA strains responsible for infections that are resistant to treatment with currently available antibiotics.

Figure 2:
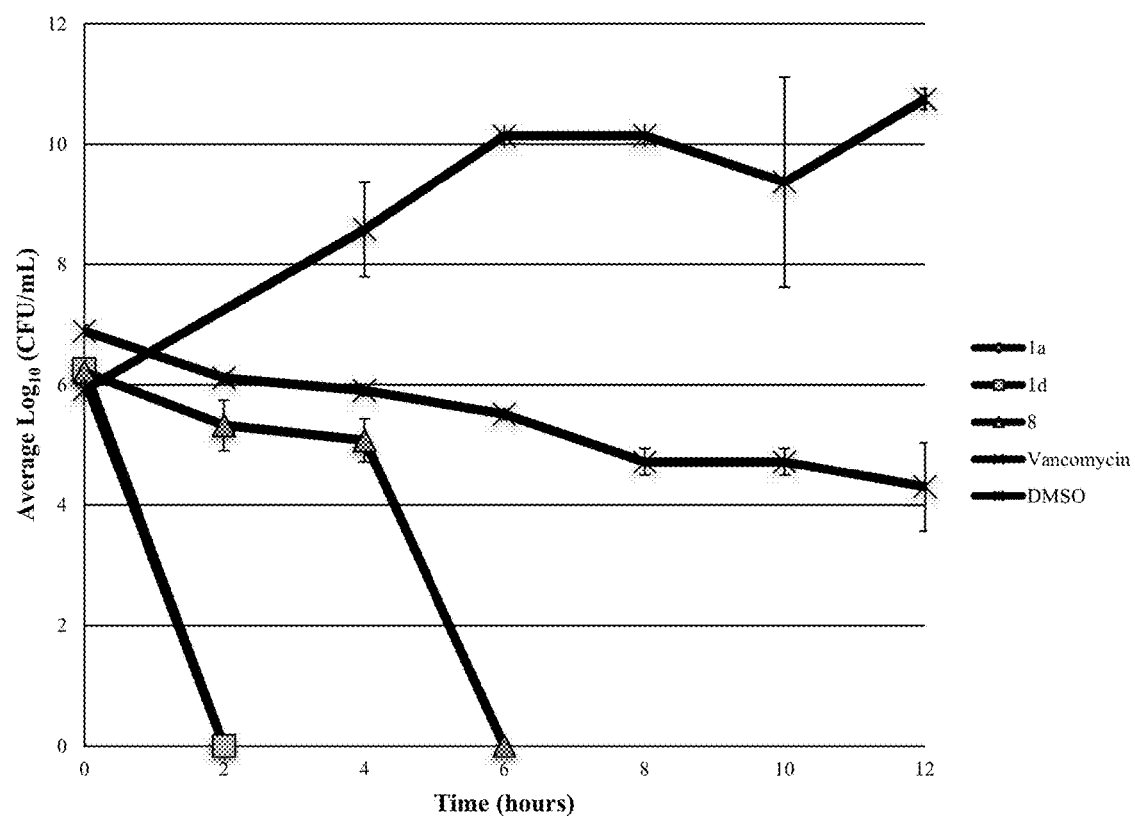
FIG. 2 is a plot of time-kill analysis of compound 1a, and derivatives 1d and 8 over time.

Time-kill analysis of thiazole compounds against MRSA. Several commercial antimicrobials used to treat MRSA infections, including vancomycin and linezolid, are either only capable of inhibiting bacterial growth but do not kill the bacteria, or they exhibit a very slow bactericidal effect, resulting in difficulty in clearing the infection. Thus a compound that demonstrates the ability to rapidly kill MRSA is highly desirable because rapid killing reduces the possibility of developing bacterial resistance/tolerance. After determining that the thiazole compounds were potent against various strains of MRSA, it was important to determine the rate at which the compounds were able to eliminate MRSA in vitro. FIG. 2 presents the rate of microbial killing by compounds 1a, 1d, 8, and vancomycin when MRSA (USA300) was exposed to 3.0×MIC of each compound over a 12 hour incubation period at 37° C. Results from the time-kill assay performed indicate that at 3.0×MIC, lead compound 1a, 1d (derivative which contains one more methylene unit in the alkyl side chain), and 8 (derivative which replaces the alkyl side chain with a cyclohexane ring) are bactericidal. However, the rate of clearance of MRSA (USA300) varies among the three compounds. Compound 1d mimics the action of compound 1a, rapidly eliminating MRSA completely within two hours. This would appear logical as compounds 1a and 1d are similar in structure; the major difference resulting from the number of methylene units contained in the alkyl side chain. Compound 8 requires more than double the time (six hours) to logarithmically reduce MRSA CFU to zero. Though compound 8 appears more potent compared to compounds 1a and 1d (when comparing MIC values), the latter two appear capable of clearing MRSA colonies (albeit at a higher concentration) more rapidly. Vancomycin was not able to reduce the number of CFU by 3-$\log_{10}$ within a 12 hours window.

Collectively this indicates the thiazole compounds possess a selective advantage over vancomycin in terms of rate of elimination of MRSA cells. This information is clinically significant as it would impact the size and timing of the dose given to patients with an infection caused by MRSA. In addition to this, combination therapy using multiple antibiotics to treat MRSA infections is commonly used in clinical practice. Antibiotics that are bacteriostatic or exhibit a slow bactericidal effect (such as vancomycin) are often paired with antibiotics exhibiting a rapid bactericidal effect (such as rifampin) in order to limit the emergence of bacterial strains with reduced susceptibility to vancomycin. As the thiazole compounds presented here exhibit a rapid bactericidal effect against MRSA, the thiazole compounds may be used with other antimicrobials, including commercial antimicrobials such as vancomycin and linezolid, in combination therapy.

Cytotoxicities of thiazole derivatives in vitro. Thiazole compounds identified as potent inhibitors of bacterial growth, were tested to assess toxicity to mammalian cells. FIG. 3 shows the results of the MTS 3-(4,5-dimethylthiazol-2-yl)-5-(3-carboxymethoxyphenyl)-2-(4-sulfophenyl)-2H-tetrazolium) assay evaluating toxicity at four different concentrations of the thiazole compounds (2 μM (FIG. 3A), 4 μM (FIG. 3B), 8 μM (FIG. 3C), and 16 μM (FIG. 3D)). The test, which assesses the viability and proliferation of the mammalian cells, confirmed that all of the compounds are selective for bacterial cell inhibition over mammalian cells at a concentration below 16 μM.

Figure 3A:
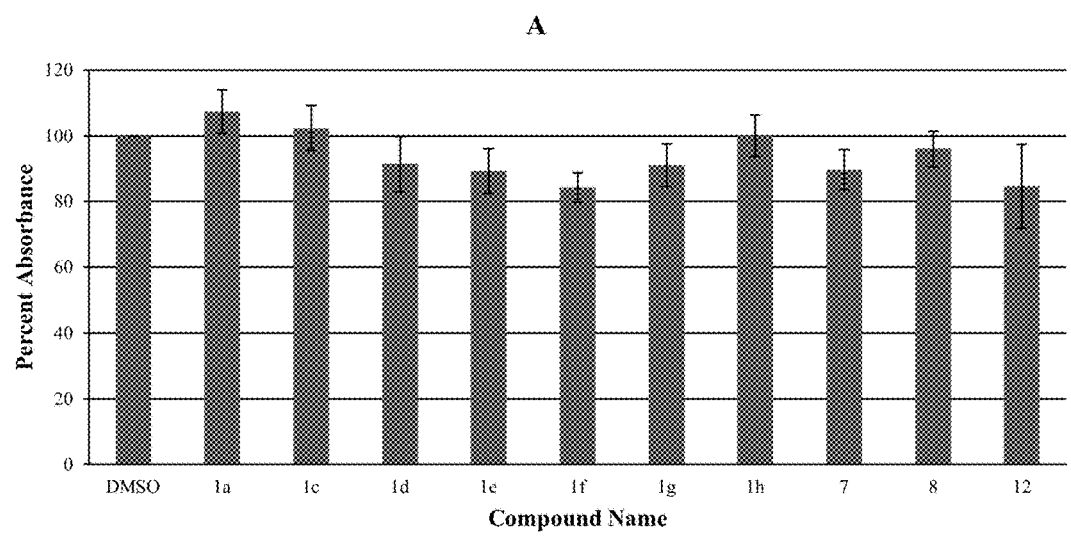
FIG. 3A-D are graphs showing results of cytotoxic analysis of thiazole compounds against murine macrophage cells (J774.A1) using the MTS assay.
Figure 3B:
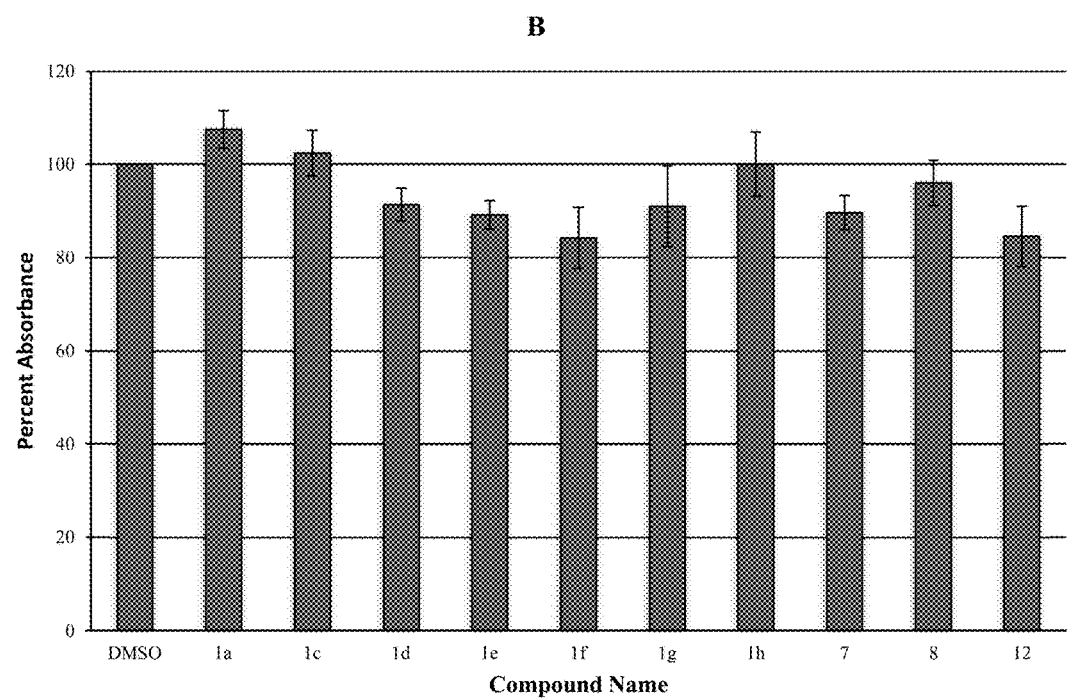
Figure 3C:
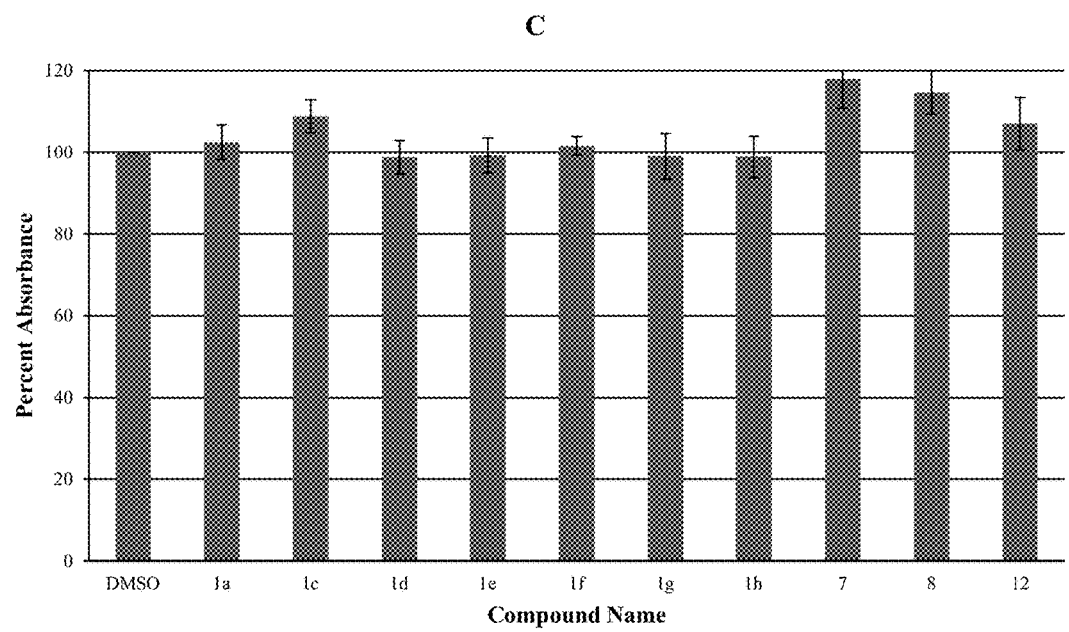
Figure 3D:
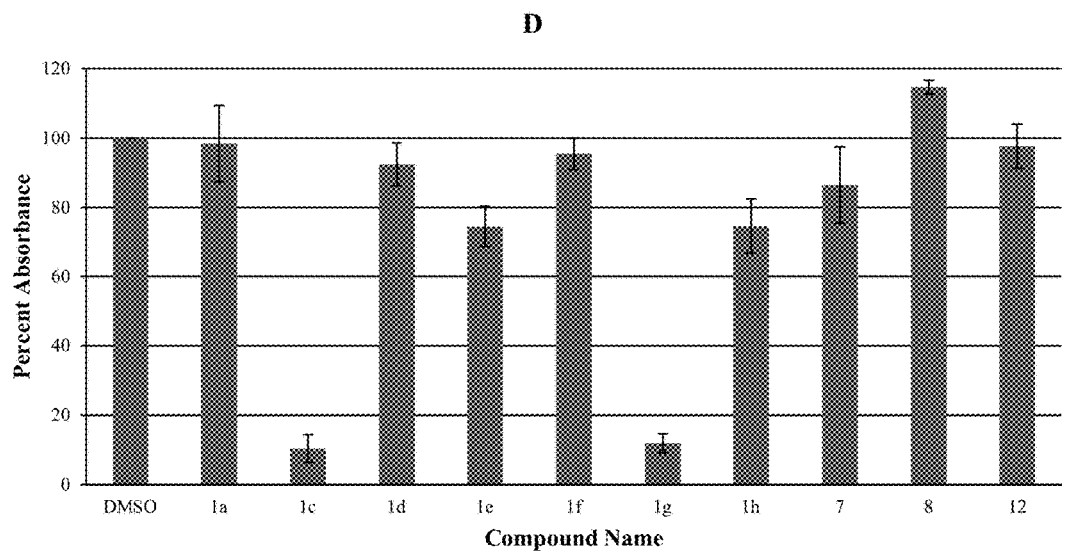

However, as can be seen from FIG. 3D, at 16 μM, four of the compounds (1c, 1e, 1g, and 1h) exhibited toxicity toward murine macrophage cells. Of the derivatives which exhibited the most potency in terms of MIC values (compounds 7, 8, and 12), none were observed to be toxic to mammalian cells. Two of the derivatives deemed toxic (compounds 1c and 1e) are have methylene units added to the linear alkyl side chain.

Changing the length of the alkyl side chain of the lead compound provides confounding results. A propyl side chain (compound 1c) results in the derivative being toxic in vitro. However, replacement of the propyl side chain with a longer alkyl moiety (from 4-5 methylene units) diminishes the cytotoxic impact. Interestingly, the addition of a sixth methylene unit to the alkyl side chain (compound 1e) results in a compound that is toxic to murine macrophage cells. Beyond seven methylene units, the derivative appears not to be toxic in vitro. Thus it would appear an ideal thiazole derivative containing the linear alkyl side chain should contain less than six methylene units to ensure the derivative is not toxic to mammalian cells.

Physicochemical properties of thiazole compounds. Physicochemical properties, including solubility and permeability, of potential therapeutic agents are critical factors that need to be explored early in drug development. Though a compound proves potent against a target organism during in vitro studies and exhibits limited toxicity to cultured mammalian cells, the drug-candidate can fail in animal and human studies if the drug is poorly soluble in aqueous solutions or is incapable of passing through cellular barriers. Analysis of the hydrogen bonding potential and lipophilicity of a compound can lend valuable insight into potential solubility and permeability issues.

After deducing the strong antimicrobial activity of the thiazole compounds and determining the limited toxicity they exhibited against murine macrophage cells, it was critical to identify if the compounds possessed potential solubility and permeability issues. Using Lipinski's Rule of 5 and TPSA as guidelines, the results in Table 3 demonstrate all ten thiazole compounds possess clog P and TPSA values that are associated with good solubility and permeability qualities. Two derivatives (1e and 1f) violate one parameter of the Rule of 5 with each derivative possessing a calculated log P value about 5. These derivatives contain the longest linear alkyl chain (six and eight methylene units for 1e and 1f, respectively) connected to the phenylthiazole nucleus. This result supports the notion that an ideal thiazole compound should consist of four methylene units in the side chain as compounds possessing an alkyl side chain with more than four methylene units exhibit a decrease in the antimicrobial activity against MRSA, present potential toxicity issues to mammalian cells, and pose potential solubility issues.

TABLE 3

Calculation of physicochemical properties of thiazole compounds for Lipinski's Rule of 5

| Compound Number | nViol | cLog P | MW | nON | nOHNH | TPSA ($Å^2$) |
|---|---|---|---|---|---|---|
| | 1 | <5 | <500 | <10 | <5 | |
| 1a | 0 | 4.23 | 346 | 5 | 4 | 87.158 |
| 1c | 0 | 3.671 | 291 | 5 | 4 | 87.158 |
| 1d | 0 | 4.735 | 274 | 5 | 4 | 87.158 |
| 1e | 1 | 5.746 | 373 | 5 | 4 | 87.158 |
| 1f | 1 | 6.756 | 275 | 5 | 4 | 87.158 |
| 1g | 0 | 4.072 | 240 | 5 | 4 | 87.158 |
| 1h | 0 | 3.549 | 240 | 5 | 4 | 87.158 |
| 7 | 0 | 4.247 | 288 | 5 | 4 | 87.158 |
| 8 | 0 | 4.727 | 366 | 5 | 4 | 87.158 |
| 12 | 0 | 4.161 | 303 | 5 | 4 | 87.158 | nViol = number of violations, cLog P = Molinspiration calculated Log P, MW = molecular weight, nON = number of hydrogen bond acceptors, nOHNH = number of hydrogen bond donors, TPSA = topological polar surface area.

Figure 4:
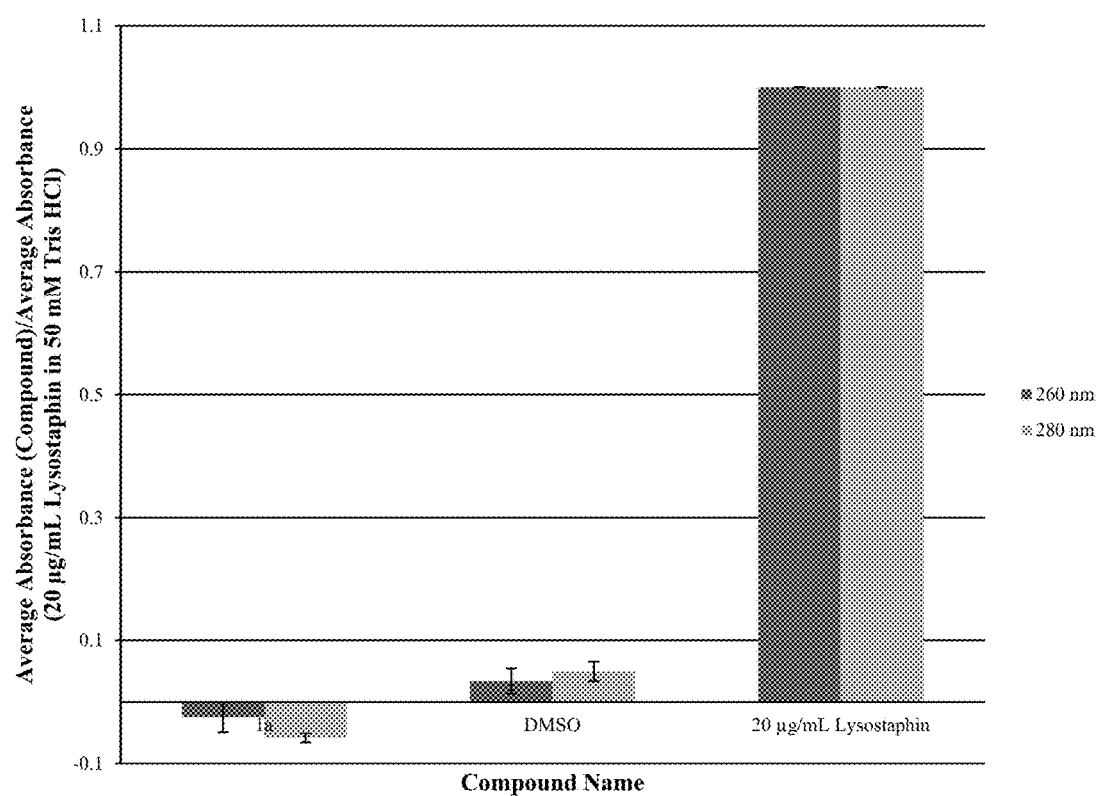
FIG. 4 shows the loss of 260 and 280 nm cellular absorbing material for compound 1a against MRSA.

Cell envelope integrity analysis and target identification. After characterizing the antimicrobial activity of the lead compound against MRSA, the thiazole compounds were evaluated to determine whether they shared the mode of action of quaternary ammonium compounds (QACs), QACs exhibit a similar general structure to the synthesized thiazole compounds and have been shown to disrupt the integrity of the bacterial cell wall, leading to leakage of intracellular content and subsequent cell death. To deduce if the thiazole compounds targeted the integrity of either the bacterial cell wall or plasma membrane, the loss of 260 and 280 nm cellular absorbing material from MRSA ATCC 43300 exposed to the lead compound 1a in vitro was utilized. Lysostaphin was used as a positive control due to its mode of action being the disruption of the cross-linking of the pentaglycin bridges in the cell wall of staphylococci bacteria. DMSO was used as a negative control. With reference to FIG. 4, when compared to the two controls, the lead thiazole compound activity aligned more closely with DMSO compared to lysostaphin, This would suggest that the antimicrobial activity of the compound is not due to disruption of the integrity of the bacterial cell wall or cytoplasmic membrane.

Figure 5:
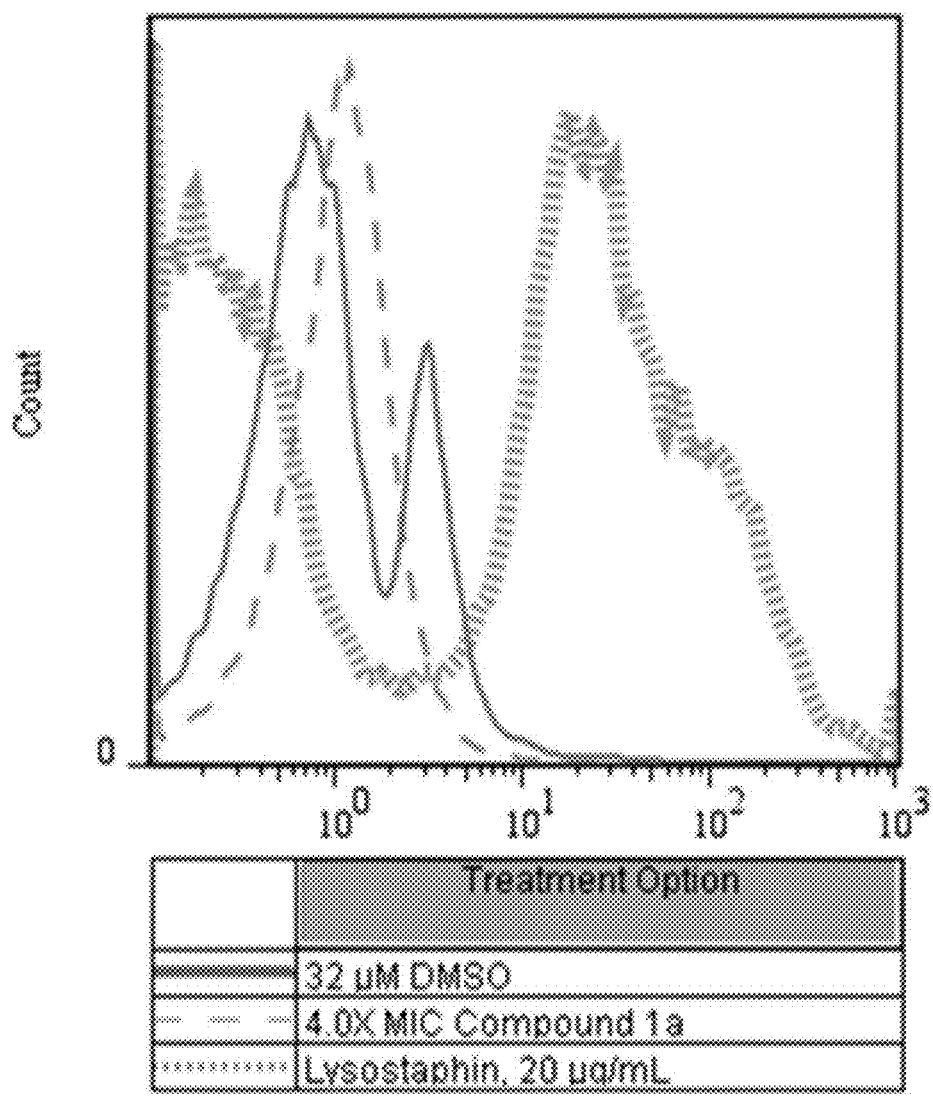
FIG. 5 is a plot showing results of an MRSA cell wall integrity analysis using LIVE/DEAD® Fixable Dead Cell Stain and flow cytometry.

To confirm this result, the LIVE/DEAD® Fixable Dead Cell Stain Kit was used in combination with flow cytometry (FIG. 5). After exposing MRSA cells to treatment with the lead compound 1a, a negative control (DMSO), and a positive control (lysostaphin), flow cytometry was used to count the number of cells which the dye was able to successfully enter and stain intracellular components in each sample. Uptake of the dye would only be possible for cells whose cell wall had become compromised during the treatment regimen. From the results obtained, treatment with DMSO resulted in 6.2% of cells being stained while treatment with lysostaphin resulted in 45% of MRSA cells becoming stained. Treatment with compound 1a at 4.0×MIC resulted in 1.5% of cells stained with the dye. This number more closely aligns with the value obtained for DMSO. The results from the flow cytometry experiment confirm the results obtained from the 260 and 280 nm cellular leakage analysis—the thiazole compounds do not target the bacterial cell envelope.

As physical disruption of the microbial cell wall or cytoplasmic membrane appears not to be the target of the presented thiazole compounds, the next step would be to identify the exact molecular target of these compounds against MRSA. Initially the mode of action of biocides with similar structural components as the presented thiazoles such as QACs, such as alkyldimethylbenzylammonium chloride (ADBAC) and didecyldimethylammonium chloride (DDAC) was investigated. However, this approach did not allow identification of the mechanism of action of the thiazole compounds. Nex, attempts were made to identify the molecular target using a target overexpression experiment in Bacillus subtilis, The obstructed metabolic function(s) in B. subtilis caused by the thiazole compound will be restored by over-expression of the targeted protein(s) through genomic insertion of a transposon with a strong outward-oriented promoter. Resistance to compound 1a is achieved by overexpression of the drug-resistance (drug$^R$) gene (where drug$^R$=molecular target or an efflux pump). In the presence of a high concentration of the thiazole compound, only bacterial colonies where the transposon successfully inserted adjacent to the biological target/resistance mechanism will be able to survive (due to overexpression of the target/resistance mechanism by the bacteria). This system identified a putative integral inner membrane protein (locus tag: BSU31160), an enzyme involved with peptidoglycan synthesis (undecaprenyl diphosphatase, locus tag: BSU31150), and a putative efflux transporter (locus tag: BSU31130) as targets of the thiazole compounds (data not published). We are currently working to validate the true target of the thiazole compounds. Confirmation of the target of the thiazole compounds will shed light into further modifications which can be made to the compounds to enhance their antimicrobial impact against MRSA. Additionally, identification of potential resistance mechanisms to the thiazole compounds that can be avoided in the compound optimization stage will assist in making the compounds less amenable to efflux and mitigate the cytotoxic properties of this newly discovered class of antibacterials.

The identification of novel antimicrobial agents to treat an array of infections caused by methicillin-resistant and vancomycin-resistant Staphylococcus aureus requires a multifold approach from whole-cell screening of chemical libraries to rational drug design. Reported herein is the exciting discovery of a lead antimicrobial compound, identified from whole-cell screening of a library of thiazole and thiadiazole compounds, that is capable of inhibiting growth of 18 strains of MRSA and VRSA. The lead compound includes a thiazole central ring connected to two structural elements critical for activity, namely a cationic element at the C5-position and a lipophilic moiety at the C2-position, A focused library of derivatives containing modifications to the lipophilic moiety was constructed to enhance the antimicrobial activity of the lead compound against MRSA and VRSA. The lead compound and nine derivatives are capable of inhibiting growth of 18 different clinical isolates of MRSA and VRSA at a concentration ranging from 0.5 to 3.0 µg/mL. Furthermore, the lead compound and two derivatives exhibit a rapid bactericidal effect, eliminating MRSA growth in vitro within six hours. This is a significant improvement over the slow bactericidal effect exhibited by vancomycin, an antibiotic commonly used to treat MRSA infections, In addition to this, six derivatives, including the three most potent compounds against MRSA, are not toxic to murine macrophage cells at a concentration of 16 µM. The ten thiazole compounds possess good solubility and permeability characteristics, meeting the criterion set forth by Lipinski's Rule of 5. Investigation of the molecular target of the compounds through cell leakage analysis revealed the lead compound does not target the integrity of the bacterial cell wall or cytoplasmic membrane. The characterization of the novel thiazole compounds presents an intriguing step in the development of a novel class of therapeutic agents effective for treating MRSA and VRSA infections.

Testing of additional compounds Additional compounds, the structures of which are shown in the Supplemental Table of Compounds, were tested for the ability to inhibit MRSA The MIC of compounds R1-R6, the parent compound (1A), and DMSO were determined using the broth microdilution (double dilution) technique (testing concentration at a range of 64 µM down to 0.5 µM) against $1.0 \times 10^5$ MRSA ATCC 43300 in a 96 well-plate at 37° C. for 19 hours (Table 4).

TABLE 4

MIC of compounds against MRSA ATCC 43300

| No. | Name | Minimum Inhibitory Concentration (µM) |
|---|---|---|
| 1A | ASM-V-22 | 4.0 |
| R1 | PVN-9-42 | 4.0 |
| R2 | PVN-9-39 | >64.0 |
| R3 | PVN-9-35 | >64.0 |
| R4 | PVN-9-34-1 | >64.0 |
| R5 | PVN-9-33-1 | >64.0 |
| R6 | PVN-9-29 | >64.0 |
| DMSO | Dimethyl Sulfoxide | No inhibition observed |

The MIC of compounds R7-R11, the parent compound (1A), and DMSO were determined using the broth microdilution (double dilution) technique (testing concentration at a range of 128 µM down to 1.0 µM) against $1.0 \times 10^5$ MRSA NRS384 (USA300) in a 96 well-plate at 37° C. for 19 hours (Table 5).

TABLE 5

MIC of compounds against MRSA NRS384

| No. | Name | Minimum Inhibitory Concentration (µM) |
|---|---|---|
| 1A | ASM-V-22 | 4.0 |
| R7 | DM 1-5 | >128.0 |
| R8 | DM 1-9-R | 128.0 |
| R9 | DM 1-9-S | 128.0 |
| R10 | DM 1-12 | 128.0 |
| R11 | PVN-9-78 | >128.0 |
| DMSO | Dimethyl Sulfoxide | No inhibition observed |

The MIC of compounds M1-M19 was determined using the broth microdilution (double dilution) technique (testing concentration at a range of 128 μM down to 1.0 μM) against MRSA ATCC 43300 in a 96 well-plate at 37° C. for 20 hours (Table 6). The minimum bactericidal concentration (MBC) for the compounds was determined by transferring 10 μL from wells where no growth was observed onto tryptic soy agar (TSA) plates and observing for growth after 20 hour incubation at 37° C. (Table 6).

TABLE 6

The MIC and the minimum bactericidal concentration (MBC) of compounds against methicillin-resistant MRSA ATCC 43300.

| No. | Compound name | MIC (μM)/MBC (μM) |
|---|---|---|
| M1 | PVN-9-80 | >128 |
| M2 | PVN-10-13 | >128 |
| M3 | PVN-10-14 | >128 |
| M4 | PVN-10-16 | >128 |
| M5 | PVN-10-20 | >128 |
| M6 | PVN-10-24 | >128 |
| M7 | PVN-10-25 | >128 |
| M8 | PVN-10-28 | >128 |
| M9 | PVN-10-29 | >128 |
| M10 | PVN-10-30 | >128 |
| M11 | PVN-10-32 | 4/8 |
| M12 | PVN-10-33 | 4/>16 |
| M13 | PVN-10-34 | 8/16 |
| M14 | PVN-10-36 | 4/8 |
| M15 | DM1-21 | >128 |
| M16 | DM1-23 | 32 |
| M17 | DM1-25 | 32 |
| M18 | DM1-26 | >128 |
| M19 | DM1-27 | >128 |
| M20 | DM 1-29 | 8 |
| M21 | DM 1-30 | >128 |
| M22 | DM 1-36 | >128 |
| M23 | DM 1-37 | >128 |
| M24 | DM 1-39 | >128 |

Six compounds (M11-M14, M16, and M17) which exhibited activity against MRSA ATCC 43300 were screened further against three additional strains of *Staphylococcus aureus* (vancomycin-intermediate [VISA] and vancomycin-resistant [VRSA]) to determine the MIC and MBC values using the same method described above (Table 7).

TABLE 7

MIC and MBC of compounds against MRSA, vancomycin-intermediate *Staphylococcus aureus* (VISA), and VRSA.

| | | Minimum Inhibitory Concentration (μM)/Minimum Bactericidal Concentration (μM) | | | |
|---|---|---|---|---|---|
| No. | Compound Name | MRSA (ATCC 43300) | VISA (NRS1) | VISA (NRS119) | VRSA (VRS10) |
| 1A | ASM-V-22 | 4 | 16 | 4 | 4 |
| M11 | PVN-10-32 | 8/8 | 8/32 | 16/32 | 16/16 |
| M12 | PVN-10-33 | 4/16 | 4/8 | 16/16 | 8/64 |
| M13 | PVN-10-34 | 8/16 | 4/8 | 16/32 | 4/16 |
| M14 | PVN-10-36 | 8/16 | 2/4 | 4/16 | 8/8 |
| M16 | DM1-23 | 32/64 | 32/64 | 64/64 | 32/128 |
| M17 | DM1-25 | 32/64 | 16/32 | 32/64 | 32/64 |
| | Vancomycin | <1 | 2 | <1 | <1 |
| DMSO | Dimethyl sulfoxide | No inhibition observed | No inhibition observed | No inhibition observed | No inhibition observed |

The MIC of compounds 1A, R1, R7, M2, M6, M8-M14, and M16 was determined using the broth microdilution (double dilution) technique (testing concentration at a range of 128 μM down to 1.0 μM) against 10 different MRSA strains in triplicates in a 96 well-plate at 37° C. for 20 hours (Table 8). The MBC for the compounds was determined by transferring 10 μL from wells where no growth was observed onto tryptic soy agar (TSA) plates and observing for growth after 20 hour incubation at 37° C. (Table 8).

TABLE 8

MIC and MBC of compounds against MRSA AND VISA

| MRSA Strain Name | MIC (μM)/MBC (μM) Compound Number | | | | | | | | | | | | | |
|---|---|---|---|---|---|---|---|---|---|---|---|---|---|---|
| | 1A | R1 | R7 | M2 | M6 | M8 | M9 | M10 | M11 | M12 | M13 | M14 | M16 | Vancomycin |
| NRS1 (VISA) | 4/8 | 2/2 | >128 | 64/128 | >128 | >128 | >128 | >128 | 16/16 | 8/8 | 8/8 | 4/4 | 128/128 | 2/2 |
| NRS19 (VISA) | 4/8 | 4/4 | >128 | 128/128 | >128 | >128 | >128 | >128 | 32/32 | 16/16 | 8/8 | 4/4 | 128/128 | <1/<1 |
| NRS37 (VISA) | 8/8 | 4/4 | >128 | 64/128 | >128 | >128 | >128 | >128 | 8/16 | 8/8 | 8/8 | 4/4 | 128/128 | 2/2 |
| NRS107 | 8/8 | 4/4 | >128 | 64/64 | >128 | >128 | >128 | >128 | 16/32 | 8/16 | 8/16 | 4/4 | 128/128 | <1/<1 |
| NRS119 | 8/8 | 4/4 | >128 | 64/64 | >128 | >128 | >128 | >128 | 16/32 | 16/32 | 16/16 | 4/4 | 128/128 | <1/<1 |
| NRS123 | 4/4 | 4/4 | >128 | 128/128 | >128 | >128 | >128 | >128 | 16/16 | 16/32 | 16/32 | 4/4 | 128/128 | 0.5/0.5 |
| NRS194 | 4/4 | 4/4 | >128 | 128/128 | >128 | >128 | >128 | >128 | 16/16 | 16/32 | 16/32 | 4/4 | 128/128 | 0.5/0.5 |
| NRS384 | 4/4 | 4/4 | >128 | 128/128 | >128 | >128 | >128 | >128 | 16/16 | 16/16 | 16/16 | 4/4 | 128/128 | 0.5/0.5 |
| NRS385 | 4/4 | 4/4 | >128 | 128/128 | >128 | >128 | >128 | >128 | 16/16 | 16/16 | 8/8 | 4/8 | 128/128 | 0.5/0.5 |
| ATCC 43300 | 4/4 | 4/4 | >128 | 128/128 | >128 | >128 | >128 | >128 | 16/16 | 16/16 | 8/8 | 4/4 | 128/128 | 0.5/0.5 |

Assessing Solubility and Permeability of Thiazole Derivatives To assess whether compounds 1A, R1, M2, and M11-M14 have good drug-like properties in terms of solubility and permeability, Lipinski's Rule of 5 was used. The Rule of 5 states that for a compound to be considered suitable for development, it must not violate more than one of the following conditions: consist of not more than five hydrogen bond donors (defined as —OH or —NH groups), consist of not more than 10 hydrogen bond acceptors (defined as —O or —N atoms), have a molecular weight not more than 500, or have a partition coefficient (log P) not greater than five. Violations to the rule can lead to poor oral bioavailability.

TABLE 9

Calculated log P, molecular weight, number of hydrogen bond donors and acceptors, and topological polar surface area (TPSA) values for thiazole compounds 1A, R1, 2M, and 11M-14M using Molinspiration software.

| Compound Number (Seleem Lab Designation) | Compound Number (Cushman Lab Designation) | Molecular weight | Calculated log P | Number OH— and NH—H— Bond Donors | Number O— and N—H— Bond Acceptors | Calculated TPSA ($Å^2$) |
|---|---|---|---|---|---|---|
| 1A | ASM-V-22 | 346 | 4.23 | 3 | 2 | 87.158 |
| R1 | PVN-9-42 | 353 | 4.509 | 4 | 5 | 87.158 |
| M2 | PVN-10-13 | 288 | 1.442 | 6** | 6 | 113.181 |
| M11 | PVN-10-32 | 391 | 4.06 | 4 | 6 | 104.229 |
| M12 | PVN-10-33 | 367 | 4.325 | 4 | 5 | 87.158 |
| M13 | PVN-10-34 | 417 | 5.057* | 4 | 5 | 87.158 |
| M14 | PVN-10-36 | 399 | 5.345* | 4 | 5 | 87.158 |

*Values above 5.0 indicate derivative has poor solubility and may not be a good candidate for further analysis.
**Values above 5 indicate potential problems with hydrogen bond formation While the disclosure is susceptible to various modifications and alternative forms, specific exemplary embodiments of the present invention have been shown by way of example in the drawings and have been described in detail. It should be understood, however, that the invention is not limited to particular embodiments disclosed, but includes all modifications, equivalents, and alternatives falling within the scope of the claims.

APPENDIX A

Supplemental Table of Compounds

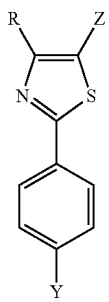

Supplemental Table of Compounds -continued

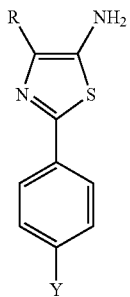

Primary Amines

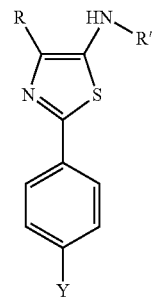

Secondary Amines

Supplemental Table of Compounds
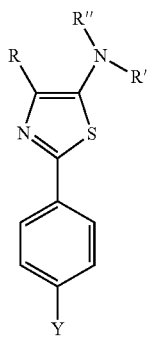
Tertiary
Amines
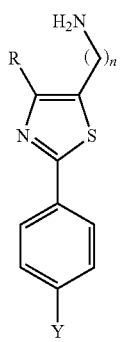
Primary
Aminoalkyl
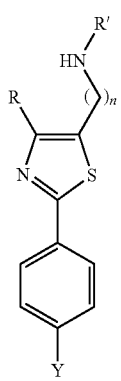
Secondary
Aminoalkyl
Supplemental Table of Compounds
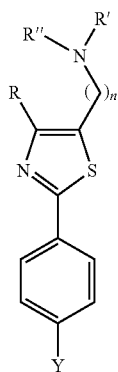
Tertiary
Aminoalkyl
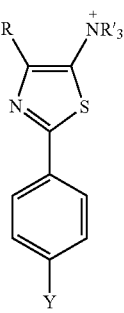
Quaternary
Ammonium
Compounds
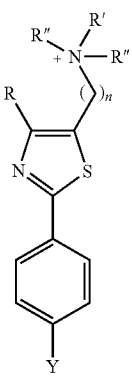
Trialkylammoniumalkyl
Compounds Supplemental Table of Compounds
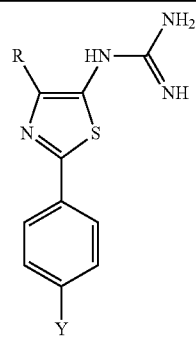
Guanidines
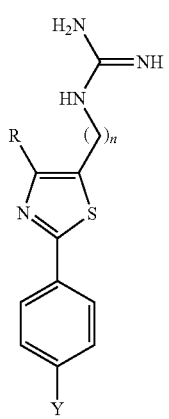
Guanidinoalkyl
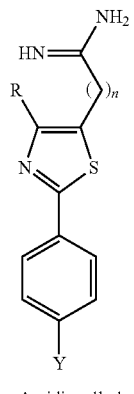
Amidinoalkyl
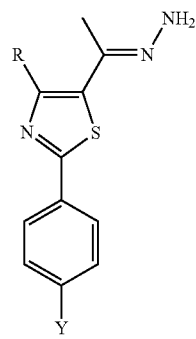
Hydrazones
Supplemental Table of Compounds
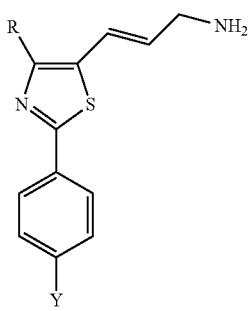
Primary Aminoalkenyl
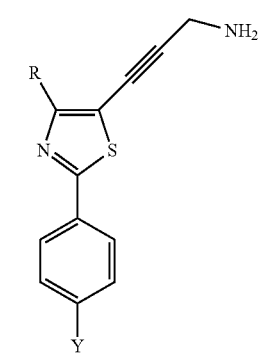
Primary Aminoalkynyl
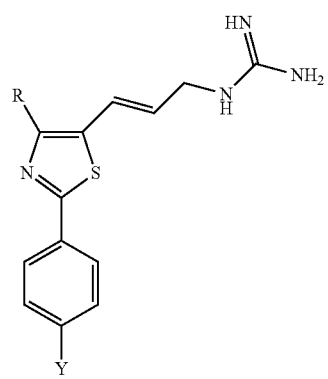
Guanidinoalkenyl Supplemental Table of Compounds
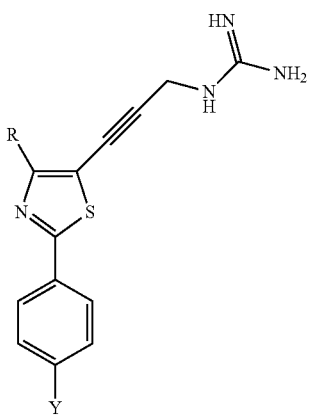
Guanidinoalkynyl
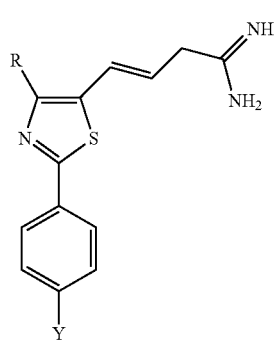
Amidinoalkenyl
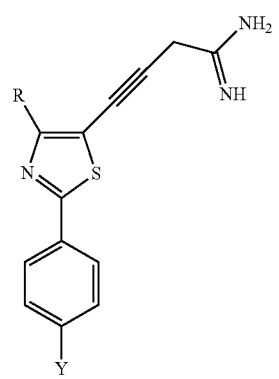
Amidinoalkynyl
Supplemental Table of Compounds
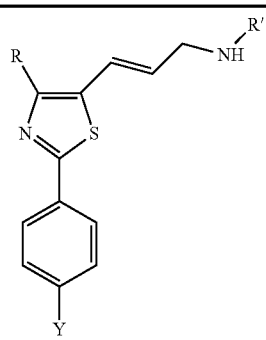
Secondary Aminoalkenyl
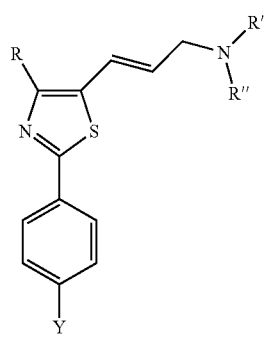
Tertiary Aminoalkenyl
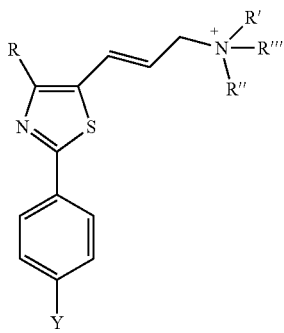
Trialkylammoniumalkenyl
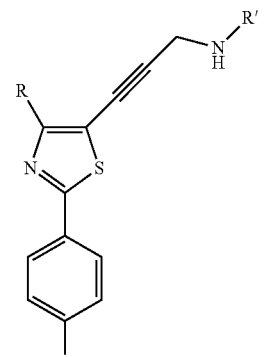
Secondary Aminoalkynyl

Supplemental Table of Compounds
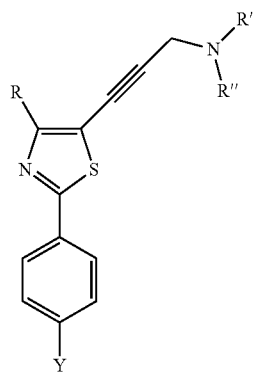
Tertiary Aminoalkynyl
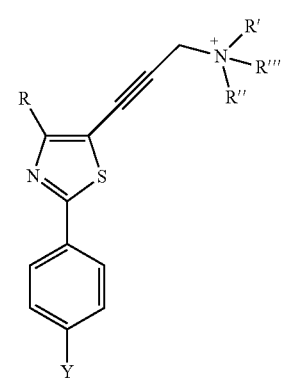
Trialkylammoniumalkynyl
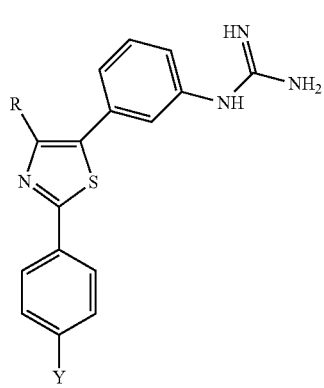
Guanidinophenyl
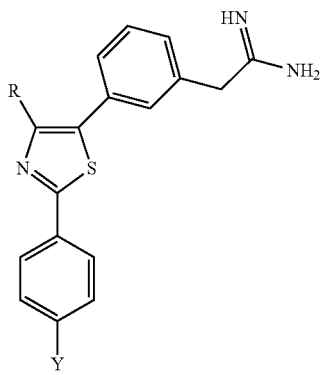
Amidinoalkylphenyl
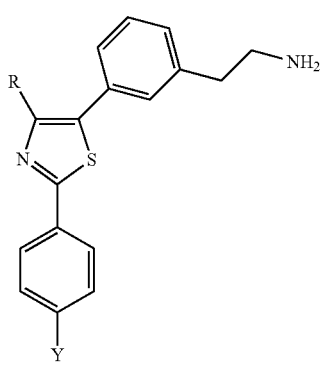
Primary Aminoalkylphenyl
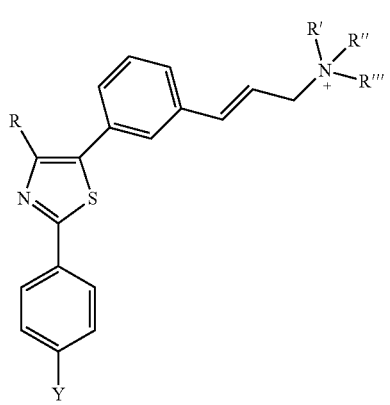
Quaternaryammoniumalkenylphenyl

Supplemental Table of Compounds
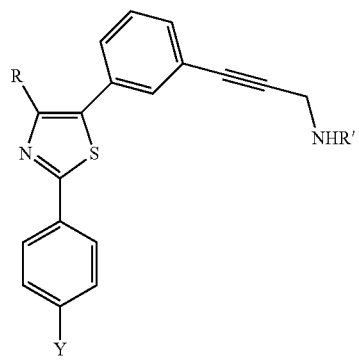
Secondary
Aminoalkynylphenyl
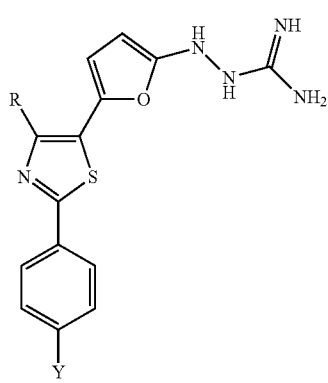
Aminoguanidinofuran
Derivative
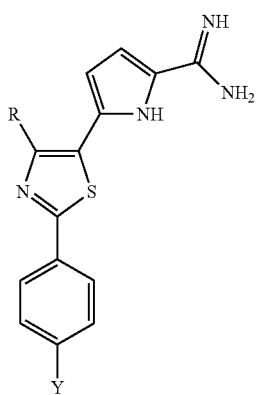
Amidinopyrrole
Derivative
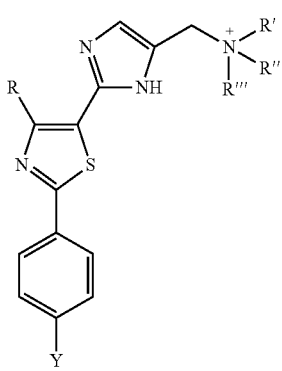
Quaternary
Aminoalkylimidazole
Derivative
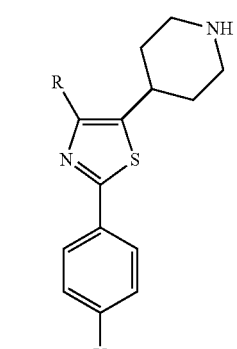
Piperidinyl
Derivative
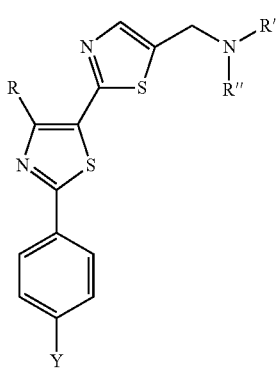
Secondary
Aminoalkylthiazole
Derivative Supplemental Table of Compounds
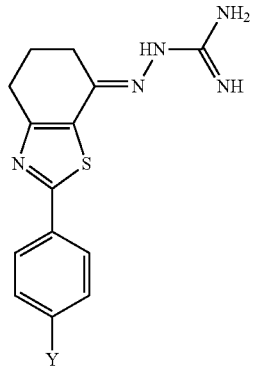
Fused Cyclic
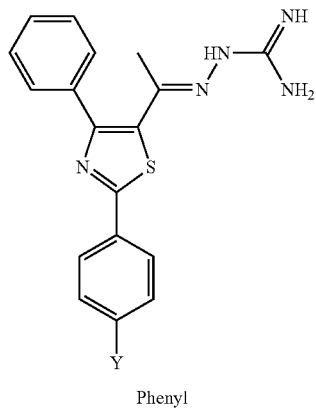
Phenyl
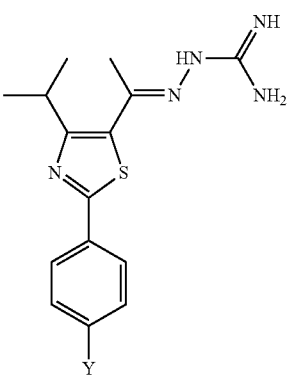
Branched Alkyl
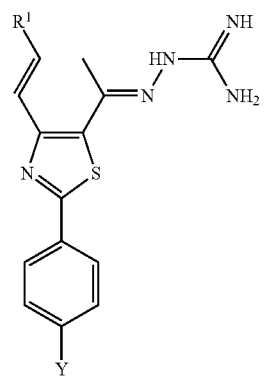
Alkenyl
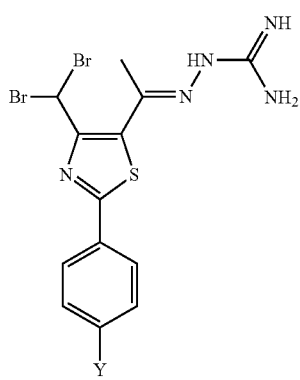
Dibromoalkyl
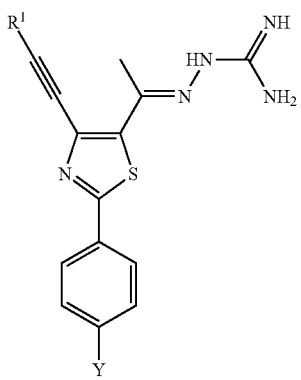
Alkynyl Supplemental Table of Compounds
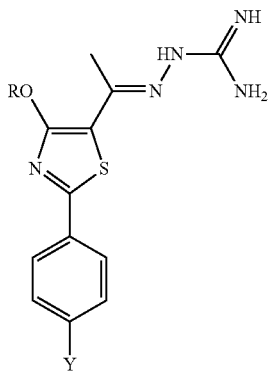
Alkoxy
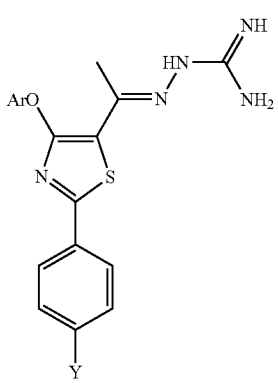
Aryloxy
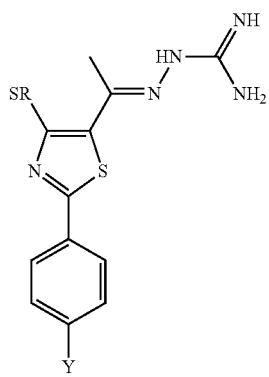
Alkylthio
Supplemental Table of Compounds
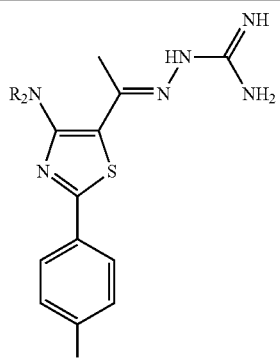
Amino
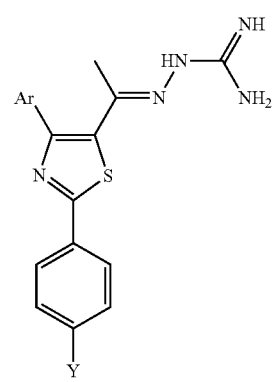
Amino
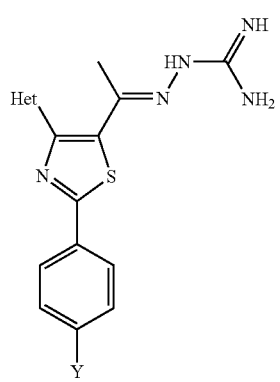
Heteroaryl
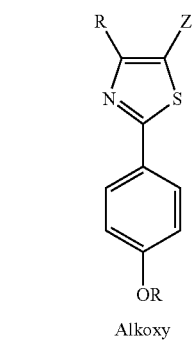
Alkoxy Supplemental Table of Compounds Aryloxy Alkylthio Arylthio Amino Heteroaryl Acyl Benzoyl Amide Supplemental Table of Compounds
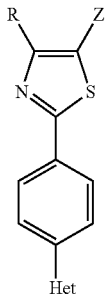
Heteroaryl
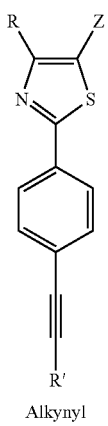
Alkynyl
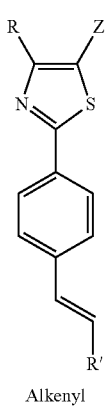
Alkenyl
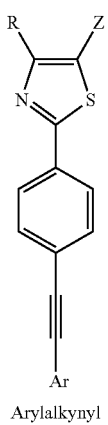
Arylalkynyl
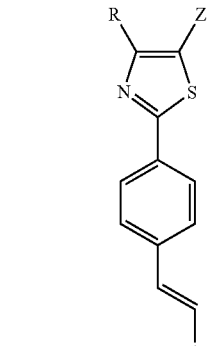
Arylalkenyl
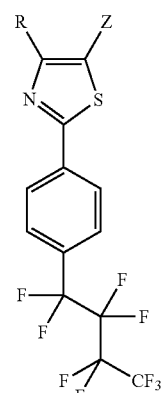
Haloalkyl
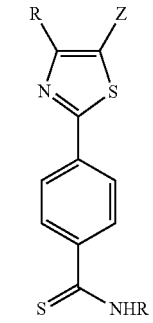
Thioamide
Z-Substitution
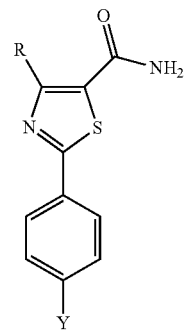

Supplemental Table of Compounds
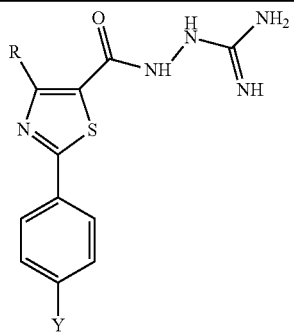
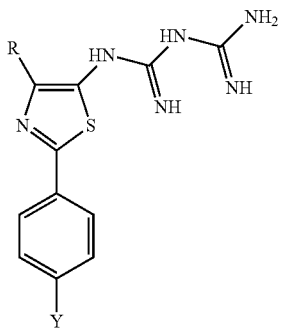
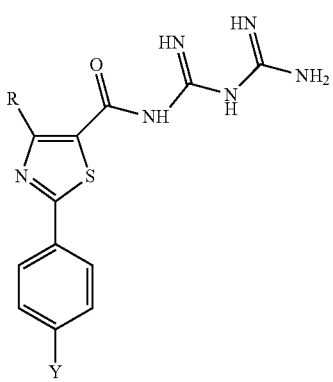
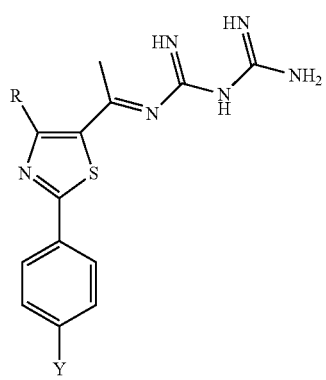
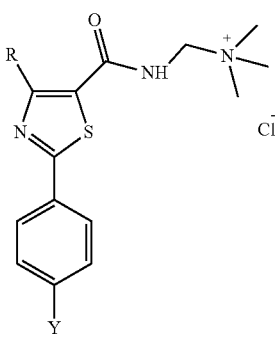
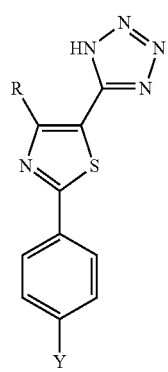
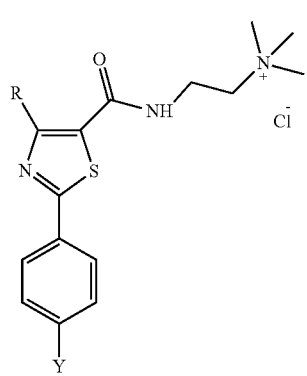
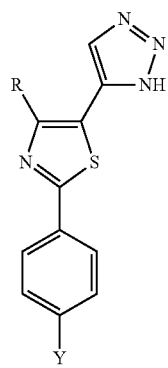

Supplemental Table of Compounds
R-Substitution
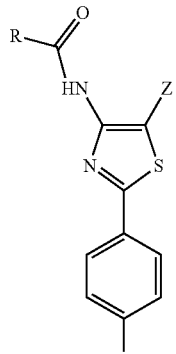
Amide
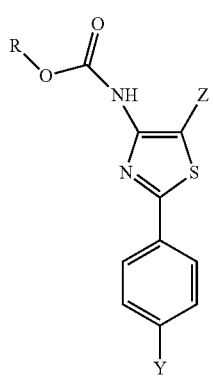
Carbamate
Y-Substitution
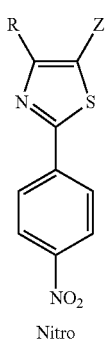
Nitro
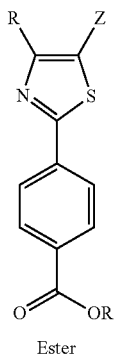
Ester
Supplemental Table of Compounds
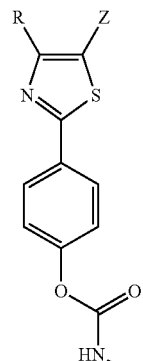
Carbamate
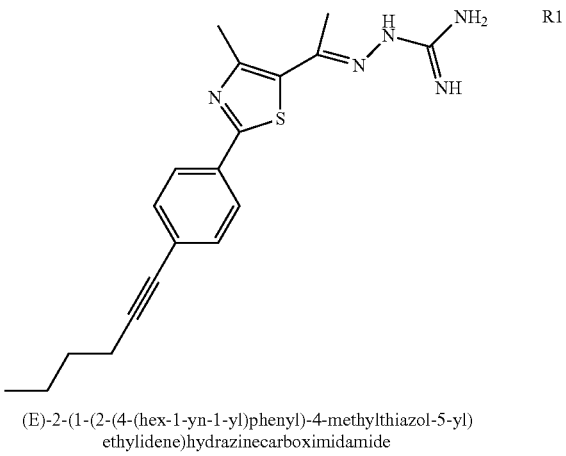
(E)-2-(1-(2-(4-(hex-1-yn-1-yl)phenyl)-4-methylthiazol-5-yl)ethylidene)hydrazinecarboximidamide   R1
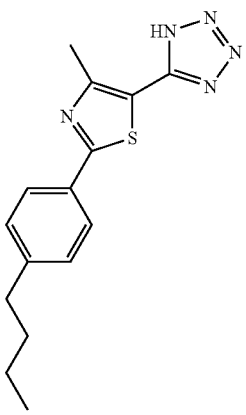
2-(4-butylphenyl)-4-methyl-5-(1H-tetrazol-5-yl)thiazole   R2

Supplemental Table of Compounds

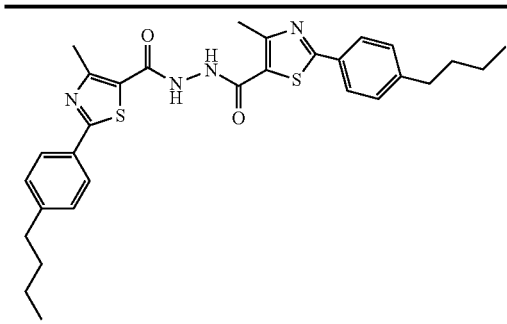

2-(4-butylphenyl)-N'-(2-(4-butylphenyl)-4-methylthiazole-5-carbonyl)-4-methylthiazole-5-carbohydrazide

R3

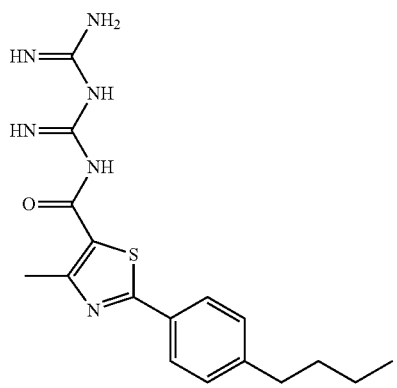

2-(4-butylphenyl)-N-(N-carbamimidoylcarbamimidoyl)-4-methylthiazole-5-carboxamide

R4

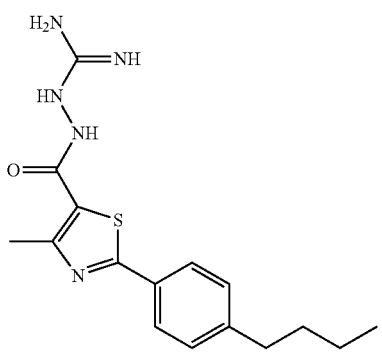

2-(2-(4-butylphenyl)-4-methylthiazole-5-carbonyl)hydrazinecarboximidamide

R5

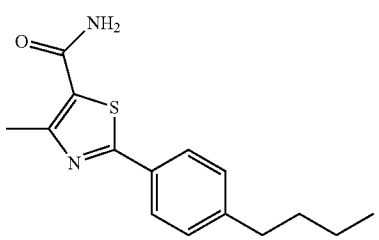

2-(4-butylphenyl)-4-methylthiazole-5-carboxamide

R6

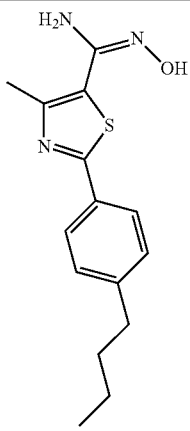

(E)-2-(4-butylphenyl)-N'-hydroxy-4-methylthiazole-5-carboximidamide

R7

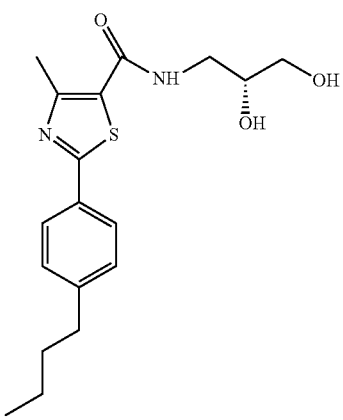

(R)-2-(4-butylphenyl)-N-(2,3-dihydroxypropyl)-4-methylthiazole-5-carboxamide

R8

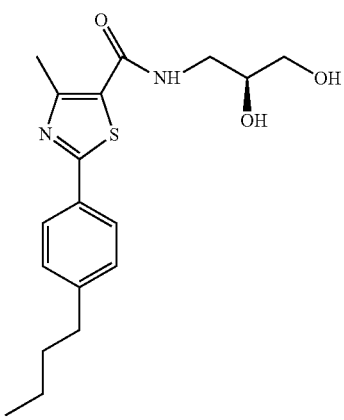

(S)-2-(4-butylphenyl)-N-(2,3-dihydroxypropyl)-4-methylthiazole-5-carboxamide

R9

Supplemental Table of Compounds
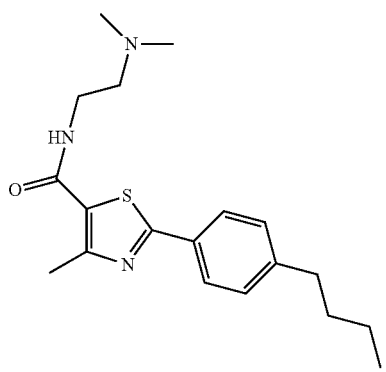
2-(4-butylphenyl)-N-(2-(dimethylamino)ethyl)-4-methylthiazole-5-carboxamide  R10
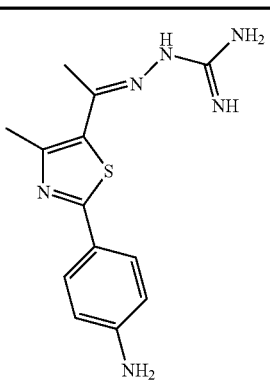
(E)-2-(1-(2-(4-aminophenyl)-4-methylthiazol-5-yl)ethylidene)hydrazinecarboximidamide  M2
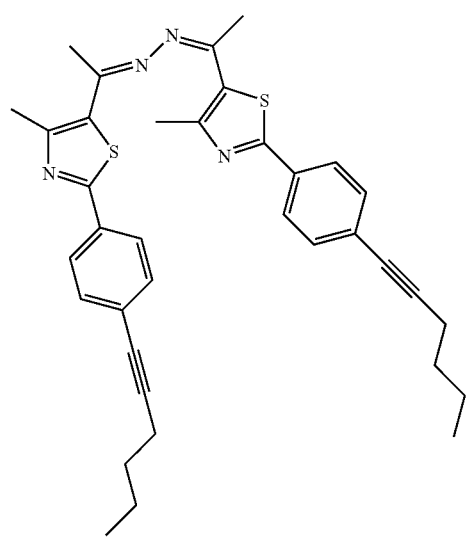
(1Z,2E)-1,2-bis(1-(2-(4-butylphenyl)-4-methylthiazol-5-yl)ethylidene)hydrazine  R11
M3
M1
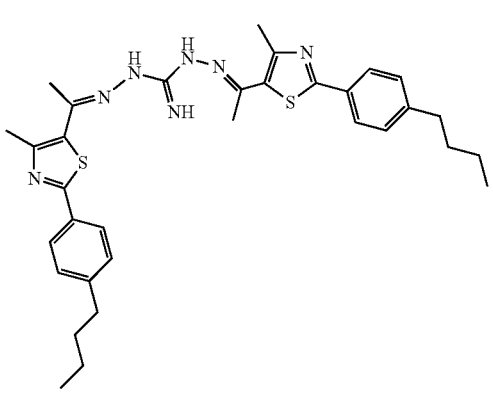 [SMILES: CCCCc1ccc(-c2nc(C)c(/C(C)=N/NC(=N)N/N=C(\C)c3sc(-c4ccc(CCCC)cc4)nc3C)s2)cc1]
1-(2-(4'-hydroxy-[1,1'-biphenyl]-4-yl)-4-methylthiazol-5-yl)ethanone  M4

Supplemental Table of Compounds
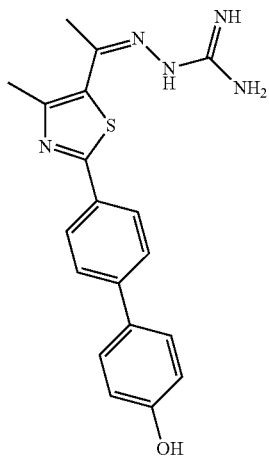
(Z)-2-(1-(2-(4'-hydroxy-[1,1'-biphenyl]-4-yl)-4-methylthiazol-5-yl)ethylidene)hydrazinecarboximidamide    M5
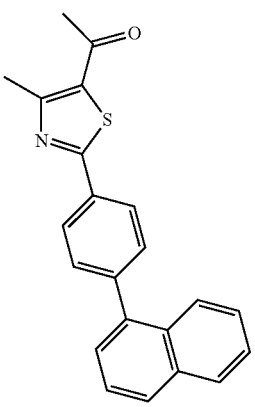
1-(4-methyl-2-(4-(naphthalen-1-yl)phenyl)thiazol-5-yl)ethanone    M6
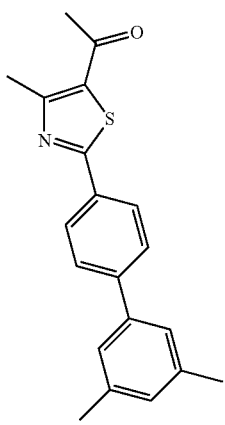
1-(2-(3',5'-dimethyl-[1,1'-biphenyl]-4-yl)-4-methylthiazol-5-yl)ethanone    M7
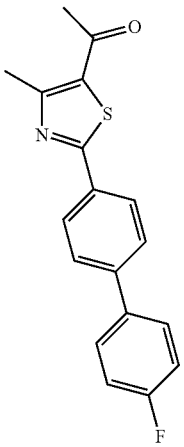
1-(2-(4'-fluoro-[1,1'-biphenyl]-4-yl)-4-methylthiazol-5-yl)ethanone    M8
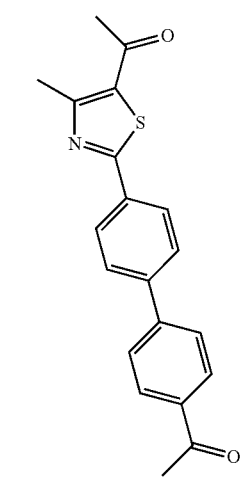
1-(4'-(5-acetyl-4-methylthiazol-2-yl)-[1,1'-biphenyl]-4-yl)ethanone    M9

Supplemental Table of Compounds

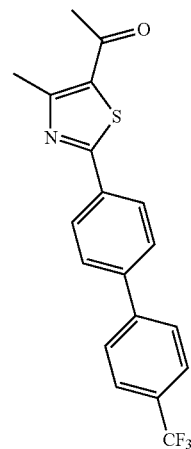

M10

1-(4-methyl-2-(4'-(trifluoromethyl-[1,1'-biphenyl]-4-yl)thiazol-5-yl)ethanone

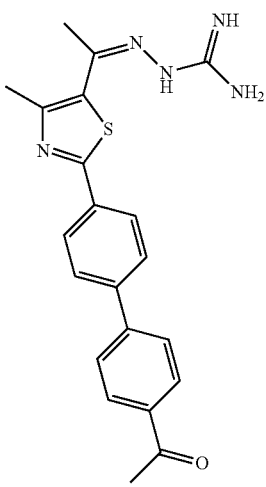

M11

(Z)-2-(1-(2-(4'-acetyl-[1,1'-biphenyl]-4-yl)-4-methylthiazol-5-yl)ethylidene)hydrazinecarboximidamide

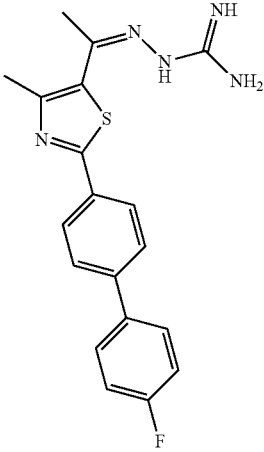

M12

(Z)-2-(1-(2-(4'-fluoro-[1,1'-biphenyl]-4-yl)-4-methylthiazol-5-yl)ethylidene)hydrazinecarboximidamide

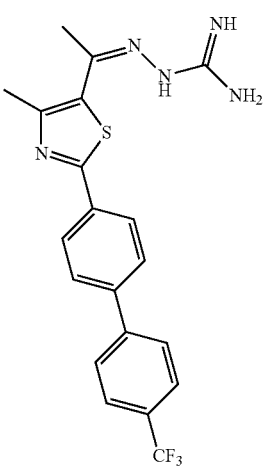

M13

(Z)-2-(1-(4-methyl-2-(4'-(trifluoromethyl)-[1,1'-biphenyl]-4-yl)thiazol-5-yl)ethylidene)hydrazinecarboximidamide

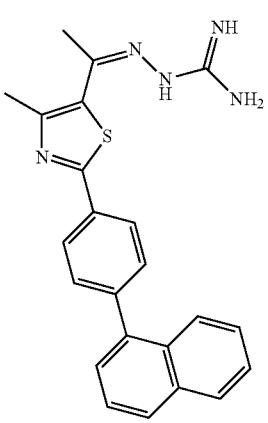

M14

(Z)-2-(1-(4-methyl-2-(4-(naphthalen-1-yl)phenyl)thiazol-5-yl)ethylidene)hydrazinecarboximidamide Supplemental Table of Compounds
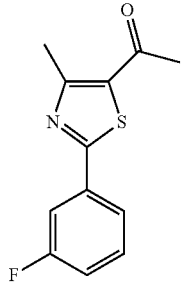
M15
1-(2-(3-fluorophenyl)-
4-methylthiazol-
5-yl)ethanone
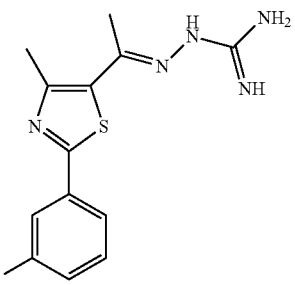
M16
(E)-2-(1-(2-(3-fluorophenyl)-4-
methylthiazol-5-yl)ethylidene)
hydrazinecarboximidamide
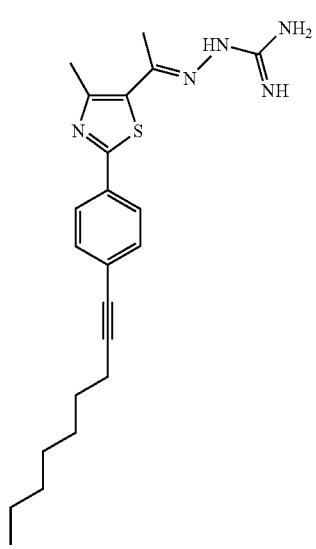
M17
(E)-2-(1-(4-methyl-2-(4-(non-1-yn-
1-yl)phenyl)thiazol-5-yl)ethylidene)
hydrazinecarboximidamide
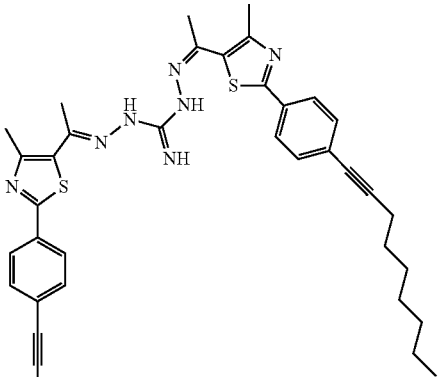
M18
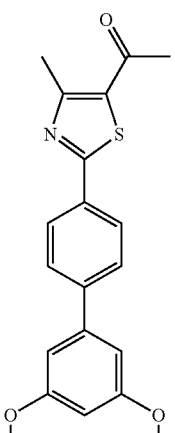
M19
1-(2-(3',5'-dimethoxy-
[1,1'-biphenyl]-4-
yl)-4-methylthiazol-
5-yl)ethanone
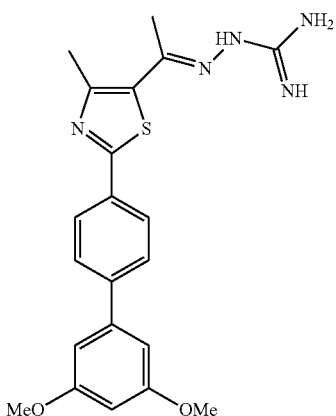 [SMILES: COc1cc(OC)cc(-c2ccc(-c3nc(C)c(/C(C)=N/NC(=N)N)s3)cc2)c1]
M20

Supplemental Table of Compounds

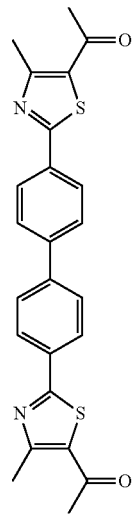

M21

1,1'-(2,2'-([1,1'-Biphenyl]-4,4'-diyl)bis(4-methylthiazole-5,2-diyl))diethanone

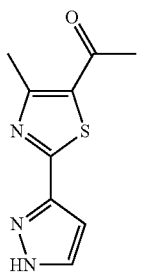

M22

1-(4-Methyl-2-(1H-pyrazol-3-yl)thiazol-5-yl)ethanone

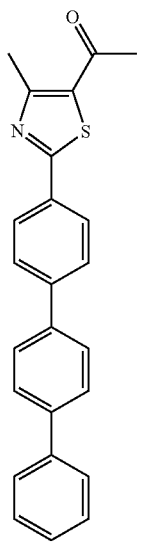

M23

1-(2-([1,1':4',1''-Terphenyl]-4-yl)-4-methylthiazol-5-yl)ethanone

Supplemental Table of Compounds

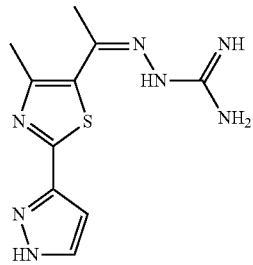

M24

(Z)-2-(1-(4-methyl-2-(1H-pyrazol-3-yl)thiazol-5-yl)ethylidene)hydrazinecarboximidamide

The invention claimed is:

1. A method of treating a bacterial infection in a subject comprising administering to the subject a pharmaceutical composition in an amount effective to treat the infection, the pharmaceutical composition comprising a compound having the chemical structure:

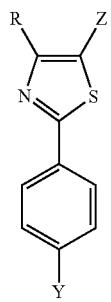

wherein Z consists of aminoguanidine, guanidine, or hydrazinecarboximidamide Y consists of cyclohexyl, cyclohexenyl or naphthyl, and R consists of methyl, wherein the compound has antibacterial activity, and wherein the compound does not substantially disrupt bacterial cell membranes.

2. The method of claim 1, wherein Z is an aminoguanidine.

3. The method of claim 1, wherein the compound is selected from a group consisting of compound 1h

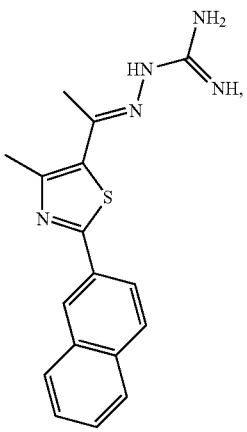

-continued compound 7

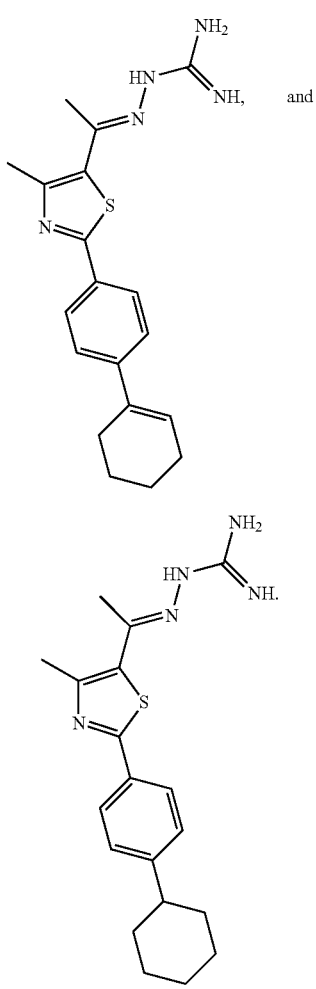

compound 8

8. The method of claim 7, wherein the subject is a human.

9. A method of treating a bacterial infection in a subject comprising administering to the subject a pharmaceutical composition in an amount effective to treat the infection, the pharmaceutical composistion comprising a compound having the chemical structure:

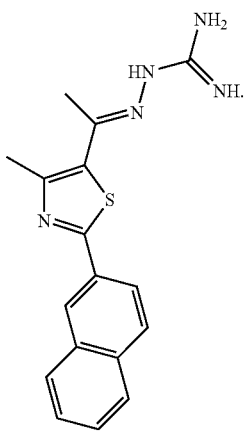 [SMILES: C/C(=N\NC(=N)N)c1sc(-c2ccc3ccccc3c2)nc1C]

10. A method of treating a bacterial infection in a subject comprising administering to the subject a pharmaceutical composition in an amount effective to treat the infection, the pharmaceutical composistion comprising a compound having the chemical structure:

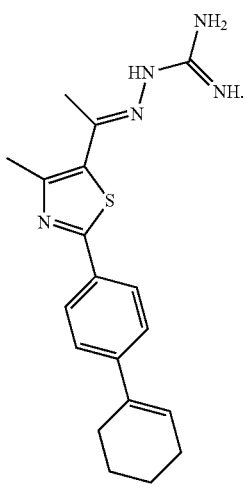 [SMILES: C/C(=N\NC(=N)N)c1sc(-c2ccc(C3=CCCCC3)cc2)nc1C]

4. The method of claim 1, wherein the compound has antibacterial activity against one or more of a MRSA, a VRSA, a *Listeria monocytogenes*, a *Bacillus anthracis*, *Bacillus subtilis*, a *Bacillus cereus*, a *Mycobacterium*, a *Streptococcus pneunomiae*, a vancomycin-resistant *Enterococcus faecalis*, *Enterococcus faecium*, and a *Candida albicans*.

5. The method of claim 4, wherein the compound has antibacterial activity against MRSA or VRSA.

6. The method of claim 1, wherein the subject is a vertebrate.

7. The method of claim 6, wherein the vertebrate is a mammal, a bird, a fish, a reptile, or an amphibian.

* * * * *